US012686864B2

(12) United States Patent
Green et al.

(10) Patent No.: US 12,686,864 B2
(45) Date of Patent: Jul. 21, 2026

(54) METHODS OF PRODUCING NUCLEIC ACID LIBRARIES AND COMPOSITIONS AND KITS FOR PRACTICING SAME

(71) Applicant: The Regents of the University of California, Oakland, CA (US)

(72) Inventors: Richard Green, Santa Cruz, CA (US); Joshua Kapp, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 70 days.

(21) Appl. No.: 18/299,553

(22) Filed: Apr. 12, 2023

(65) Prior Publication Data

US 2023/0242907 A1      Aug. 3, 2023

Related U.S. Application Data

(62) Division of application No. 17/058,066, filed as application No. PCT/US2019/035617 on Jun. 5, 2019, now Pat. No. 11,629,345.

(Continued)

(51) Int. Cl.
*C12N 15/10* (2006.01)
*C12Q 1/6869* (2018.01)

(52) U.S. Cl.
CPC ....... *C12N 15/1093* (2013.01); *C12Q 1/6869* (2013.01)

(58) Field of Classification Search
CPC .......................... C12N 15/1093; C12Q 1/6869

(Continued)

(56) References Cited

U.S. PATENT DOCUMENTS 5,744,306 A     4/1998  Murtagh et al.
6,013,438 A     1/2000  Didenko et al.
(Continued)

FOREIGN PATENT DOCUMENTS

CN        105441429        3/2016
CN        108060191        5/2018
(Continued)

OTHER PUBLICATIONS

Prediger, Ellen. Oligo modifications that block nuclease degradation. [online]. Integrated DNA Technologies, 2014 [retrieved on Dec. 23, 2024]. Retrieved from the Internet: <URL:https://www.idtdna.com/pages/education/decoded/article/modification-highlight-modifications-that-block-nuclease-degradation> (Year: 2014).*

(Continued)

*Primary Examiner* — Aaron A Priest
*Assistant Examiner* — Randi Lynn Beil
(74) *Attorney, Agent, or Firm* — Brian E. Davy; Bozicevic, Field & Francis LLP

(57) ABSTRACT

Provided are methods of producing nucleic acid libraries. The methods include combining single-stranded nucleic acid binding protein-bound single-stranded nucleic acid (SSB-bound ssNA), an adapter oligonucleotide, and a splint oligonucleotide, to form complexes including the splint oligonucleotide hybridized to a terminal region of the SSB-bound ssNA and to the adapter oligonucleotide. An end of the first adapter oligonucleotide is adjacent to an end of the first terminal region of the SSB-bound ssNA, and the methods may further include covalently linking the adjacent ends. Also provided are compositions and kits that find use, e.g., in practicing the methods of the present disclosure.

15 Claims, 6 Drawing Sheets

Specification includes a Sequence Listing.

Related U.S. Application Data

(60) Provisional application No. 62/681,524, filed on Jun. 6, 2018.

(58) Field of Classification Search
USPC .......................................................... 506/2
See application file for complete search history.

(56) References Cited

U.S. PATENT DOCUMENTS

| | | | |
|---|---|---|---|
| 6,057,101 | A | 5/2000 | Nandabalan et al. |
| 6,261,774 | B1 | 7/2001 | Pagratis et al. |
| 6,261,782 | B1 | 7/2001 | Lizardi et al. |
| 6,607,878 | B2 | 8/2003 | Sorge |
| 6,670,120 | B1 | 12/2003 | Schmidt et al. |
| 6,677,121 | B2 | 1/2004 | Lizardi et al. |
| 6,773,886 | B2 | 8/2004 | Kaufman et al. |
| 6,927,028 | B2 | 8/2005 | Dennis et al. |
| 7,166,429 | B2 | 1/2007 | Van Eijk et al. |
| 7,169,561 | B2 | 1/2007 | Spier |
| 7,282,335 | B2 | 10/2007 | Gocke et al. |
| 7,588,896 | B2 | 9/2009 | Spier |
| 7,723,077 | B2 | 5/2010 | Young et al. |
| 7,741,463 | B2 | 6/2010 | Gormley et al. |
| 7,838,647 | B2 | 11/2010 | Hahn et al. |
| 8,034,568 | B2 | 10/2011 | Kurn et al. |
| 8,053,192 | B2 | 11/2011 | Bignell et al. |
| 8,071,311 | B2 | 12/2011 | Kurn |
| 8,071,312 | B2 | 12/2011 | Makarov et al. |
| 8,168,388 | B2 | 5/2012 | Gormley et al. |
| 8,192,941 | B2 | 6/2012 | Kuersten |
| 8,206,901 | B2 | 6/2012 | Freskgard et al. |
| 8,420,319 | B2 | 4/2013 | Mikawa |
| 8,563,478 | B2 | 10/2013 | Gormley et al. |
| 8,575,071 | B2 | 11/2013 | Lau et al. |
| 8,664,164 | B2 | 3/2014 | Ericsson et al. |
| 8,809,518 | B2 | 8/2014 | Hayashizaki |
| 8,822,150 | B2 | 9/2014 | Bignell et al. |
| 8,828,688 | B2 | 9/2014 | Namsaraev |
| 8,932,816 | B2 | 1/2015 | Kuersten |
| 8,932,994 | B2 | 1/2015 | Gormley et al. |
| 9,109,248 | B2 | 8/2015 | Freskgard et al. |
| 9,115,352 | B2 | 8/2015 | Van den Brulle et al. |
| 9,212,378 | B2 | 12/2015 | Choi et al. |
| 9,255,265 | B2 | 2/2016 | Stephens et al. |
| 9,416,406 | B2 | 8/2016 | Kuersten |
| 9,458,493 | B2 | 10/2016 | Lexow |
| 9,487,775 | B2 | 11/2016 | Franch et al. |
| 9,506,055 | B2 | 11/2016 | Lau et al. |
| 9,506,113 | B2 | 11/2016 | Eshoo et al. |
| 9,546,399 | B2 | 1/2017 | Amorese et al. |
| 9,580,751 | B2 | 2/2017 | Hahn et al. |
| 9,605,313 | B2 | 3/2017 | Cantor et al. |
| 9,624,534 | B2 | 4/2017 | Kuersten |
| 9,631,227 | B2 | 4/2017 | Paul et al. |
| 9,695,469 | B2 | 7/2017 | De Boer et al. |
| 9,745,627 | B2 | 8/2017 | van Eijk et al. |
| 9,765,375 | B2 | 9/2017 | Murray et al. |
| 9,783,799 | B2 | 10/2017 | Kim et al. |
| 9,816,120 | B2 | 11/2017 | Bevilacqua et al. |
| 9,834,816 | B2 | 12/2017 | Kuersten |
| 9,834,822 | B2 | 12/2017 | Talasaz |
| 9,885,035 | B2 | 2/2018 | Franch et al. |
| 9,890,375 | B2 | 2/2018 | Geng et al. |
| 9,914,958 | B2 | 3/2018 | Wong et al. |
| 9,920,360 | B2 | 3/2018 | Wong et al. |
| 9,951,384 | B2 | 4/2018 | Schnable et al. |
| 9,982,255 | B2 | 5/2018 | Varley et al. |
| 10,011,866 | B2 | 7/2018 | Eshoo et al. |
| 10,011,870 | B2 | 7/2018 | Zimmermann et al. |
| 10,017,807 | B2 | 7/2018 | Srinivasan et al. |
| 10,047,359 | B2 | 8/2018 | Stephens et al. |
| 10,144,962 | B2 | 12/2018 | Larson et al. |
| 10,155,976 | B2 | 12/2018 | Jones et al. |
| 10,227,587 | B2 | 3/2019 | Zhang et al. |
| 10,240,191 | B2 | 3/2019 | Kuersten |
| 10,316,357 | B2 | 6/2019 | Makarov et al. |
| 11,629,345 | B2 | 4/2023 | Green et al. |
| 2002/0058256 | A1 | 5/2002 | Rothberg et al. |
| 2002/0106649 | A1 | 8/2002 | Lizardi et al. |
| 2002/0142309 | A1 | 10/2002 | Dattagupta |
| 2003/0082556 | A1 | 5/2003 | Kaufman et al. |
| 2003/0104363 | A1 | 6/2003 | Arguello et al. |
| 2003/0165923 | A1 | 9/2003 | Li et al. |
| 2003/0165963 | A1 | 9/2003 | Dattagupta |
| 2003/0219878 | A1 | 11/2003 | Lindbo et al. |
| 2004/0006033 | A1 | 1/2004 | Zhu |
| 2004/0265888 | A1 | 12/2004 | Kaufman et al. |
| 2005/0272075 | A1 | 12/2005 | Jacobsen et al. |
| 2006/0024738 | A1 | 2/2006 | Rabbani et al. |
| 2008/0160511 | A1 | 7/2008 | Dawson et al. |
| 2009/0317818 | A1 | 12/2009 | Ehrich et al. |
| 2010/0105049 | A1 | 4/2010 | Ehrich et al. |
| 2010/0311602 | A1 | 12/2010 | Levy et al. |
| 2011/0076675 | A1 | 3/2011 | Jacobsen et al. |
| 2011/0319290 | A1 | 12/2011 | Raymond et al. |
| 2012/0142060 | A1 | 6/2012 | Makarov et al. |
| 2012/0329054 | A1 | 12/2012 | Dawson et al. |
| 2013/0005585 | A1 | 1/2013 | Anderson et al. |
| 2013/0012399 | A1 | 1/2013 | Myers et al. |
| 2013/0303407 | A1 | 11/2013 | Makarov et al. |
| 2013/0338011 | A1 | 12/2013 | Dawson et al. |
| 2014/0066335 | A1 | 3/2014 | Gormley et al. |
| 2014/0123182 | A1 | 5/2014 | Lee et al. |
| 2014/0329698 | A1 | 11/2014 | Bignell et al. |
| 2015/0004604 | A1 | 1/2015 | Eshoo et al. |
| 2015/0051088 | A1 | 2/2015 | Kim |
| 2015/0132763 | A1 | 5/2015 | Amorese et al. |
| 2015/0203906 | A1 | 7/2015 | Betts et al. |
| 2016/0032396 | A1 | 2/2016 | Diehn et al. |
| 2016/0034019 | A1 | 2/2016 | Seo et al. |
| 2016/0057193 | A1 | 2/2016 | Yun |
| 2016/0083720 | A1 | 3/2016 | Freskgard et al. |
| 2016/0177380 | A1 | 6/2016 | Ruan |
| 2016/0194628 | A1 | 7/2016 | Stephens et al. |
| 2016/0340746 | A1 | 11/2016 | Makarov et al. |
| 2016/0355880 | A1 | 12/2016 | Gormley et al. |
| 2017/0101674 | A1 | 4/2017 | So et al. |
| 2017/0145499 | A1 | 5/2017 | Bignell et al. |
| 2017/0218979 | A1 | 8/2017 | Kim |
| 2018/0002731 | A1 | 1/2018 | Wu et al. |
| 2018/0002749 | A1 | 1/2018 | Larson et al. |
| 2018/0016631 | A1 | 1/2018 | van Eijk et al. |
| 2018/0051328 | A1 | 2/2018 | Kuersten |
| 2018/0087108 | A1 | 3/2018 | Berka et al. |
| 2018/0142235 | A1 | 5/2018 | Zhang et al. |
| 2018/0230516 | A1 | 8/2018 | Gu et al. |
| 2019/0093102 | A1 | 3/2019 | Jung et al. |
| 2019/0194649 | A1 | 6/2019 | Raine et al. |
| 2020/0149098 | A1 | 5/2020 | Green |
| 2021/0010081 | A1 | 1/2021 | Shendure et al. |
| 2021/0054366 | A1 | 2/2021 | Harkins Kincaid et al. |
| 2021/0222161 | A1 | 7/2021 | Green et al. |
| 2022/0348906 | A1 | 11/2022 | Harkins Kincaid et al. |
| 2023/0235320 | A1 | 7/2023 | Troll et al. |
| 2023/0242907 | A1 | 8/2023 | Green et al. |

FOREIGN PATENT DOCUMENTS

| | | |
|---|---|---|
| CN | 109563543 | 4/2019 |
| CN | 112243462 | 1/2021 |
| KR | 20110095604 A | 8/2011 |
| KR | 20160120260 A | 10/2016 |
| WO | WO 1989001526 | 2/1989 |
| WO | WO 1997027330 | 7/1997 |
| WO | WO 1997046704 | 12/1997 |
| WO | WO 2000039333 | 7/2000 |
| WO | WO 2006056480 | 6/2006 |
| WO | WO 2007140417 | 12/2007 |
| WO | WO 2007147063 | 12/2007 |
| WO | WO 2009032779 | 3/2009 |
| WO | WO 2009032781 | 3/2009 |
| WO | WO 2010033639 | 3/2010 |
| WO | WO 2010115016 | 10/2010 |
| WO | WO 2011034631 | 3/2011 |

(56) References Cited

FOREIGN PATENT DOCUMENTS

| | | | | |
|---|---|---|---|---|
| WO | WO 2011143659 | 11/2011 | | |
| WO | WO 2011156529 | 12/2011 | | |
| WO | 2012104261 | 8/2012 | | |
| WO | WO 2012103154 | 8/2012 | | |
| WO | 2013036810 | 3/2013 | | |
| WO | 2013191775 | 12/2013 | | |
| WO | WO-2014071322 A1 * | 5/2014 | ............. | C12P 19/34 |
| WO | WO 2014164466 | 10/2014 | | |
| WO | WO 2014210353 | 12/2014 | | |
| WO | WO 2015118077 | 8/2015 | | |
| WO | 2015140307 | 9/2015 | | |
| WO | WO 2015134552 | 9/2015 | | |
| WO | 2016044227 | 3/2016 | | |
| WO | WO 2016058517 | 4/2016 | | |
| WO | WO 2016081798 | 5/2016 | | |
| WO | WO 2016156529 | 10/2016 | | |
| WO | 2017112666 | 6/2017 | | |
| WO | WO 2017205540 | 11/2017 | | |
| WO | 2017218979 | 12/2017 | | |
| WO | WO 2017210469 | 12/2017 | | |
| WO | WO 2018013837 | 1/2018 | | |
| WO | WO 2018140695 | 8/2018 | | |
| WO | WO 2018175258 | 9/2018 | | |
| WO | WO 2018175997 | 9/2018 | | |
| WO | WO 2019140201 | 7/2019 | | |
| WO | 2019222523 | 11/2019 | | |
| WO | 2019237032 | 12/2019 | | |
| WO | WO 2019236726 | 12/2019 | | |
| WO | WO 2020206143 | 10/2020 | | |
| WO | 2021262805 | 12/2021 | | |
| WO | 2021050393 | 3/2024 | | |
| WO | 2024054517 | 3/2024 | | |

OTHER PUBLICATIONS

Caroe, et al. (2017) "Single-tube library preparation for degraded DNA", Methods in Ecology and Evolution, 9(2), vol. 9, Issue 2, pp. 410-419.

Genbank, "DNA polymerase [*Thermococcus* sp. 9oN-7]", Genbank accession No. AAA88769.1, Nov. 9, 2001, 2 pages.

Mak, et al. (2017) "Comparative performance of the BGISEQ-500 vs Illumina HiSeq2500 sequencing platforms for palaeogenomic sequencing", Gigascience, vol. 6, Issue 8, pp. 1-13.

Adey et al. (2010) "Rapid, Low-Input, Low-Bias Construction of Shotgun Fragment Libraries by High-Density in Vitro Transposition", Genome Biology, 11:R119 17 pages.

Altschul et al. (1997) "Gapped BLAST and PSI-BLAST: A New Generation of Protein Database Search Programs", Nucleic Acids Research 25:17 3389-3402.

Ansari et al. (1993) "In Situ End-Labelling Detects DNA Strand Breaks in Apoptosis and Other Physiological and Pathological States", The Journal of Pathology 170: 1-8.

Aravanis et al. (2017) "Next-Generation Sequencing of Circulating Tumor DNA for Early Cancer Detection", Cell 168: 571-574.

Aymard et al. (2014) "Transcriptionally Active Chromatin Recruits Homologous Recombination at DNA Double-Strand Breaks", Nature Structural & Molecular Biology 21: 366-374.

Barra et al. (2015) "EDTA-Mediated Inhibition of DNases Protects Circulating Cell-Free DNA from Ex Vivo Degradation in Blood Samples", Clinical Biochemistry 48: 976-981.

Budowle et al. (2008) "Forensically Relevant SNP Classes", BioTechniques 44:5 603-610.

Butler et al. (2003) "The Development of Reduced Size STR Amplicons as Tools for Analysis of Degraded DNA", Journal of Forensic Sciences, 42:5 1054-1064.

Butler (2019) "Fundamentals of Forensic DNA Typing", 519 pages.

Cahill et al. (2013) "Genomic Evidence for Island Population Conversion Resolves Conflicting Theories of Polar Bear Evolution", PLOS Genetics, 9:3 8 pages.

Canela et al. (2016) "DNA Breaks and End Resection Measured Genome-wide by End Sequencing", Molecular Cell 63:5 898-911.

Chan et al. (2016) "Second Generation Noninvasive Fetal Genome Analysis Reveals De Novo Mutations, Single-Base Parental Inheritance, and Preferred DNA Ends", Proceedings of the National Academy of Sciences 113: E8159-E8168.

Chitrabamrung et al., (1981) "Serum Deoxyribonuclease I and Clinical Activity in Systemic Lupus Erythematosus", Rheumatology International, 1: 55-60.

COLLINS (2004) "The Comet Assay for DNA Damage and Repair: Principles, Applications, and Limitation", Molecular Biotechnology 26: 249-261.

Crawford et al. (2006) "DNase-Chip: A High-Resolution Method to Identify DNase I Hypersensitive Sites Using Tiled Microarrays", Nature Methods 3:7 503-509.

Cristiano et al. (2019) "Genome-Wide Cell-Free DNA Fragmentation in Patients with Cancer", Nature, 570: 385-389.

Crosetto et al., (2013) "Nucleotide-Resolution DNA Double-Strand Breaks Mapping by Next-Generation Sequencing", Nature Methods, Apr. 2013, 10(4):361-365.

Crowley et al. (2013) "Liquid Biopsy: Monitoring Cancer-Genetics in the Blood", Nature Reviews Clinical Oncology 13 pages.

Dabney et al. (2013) "Complete Mitochondrial Genome Sequence of a Middle Pleistocene Cave Bear Reconstructed from Ultrashort DNA Fragments", Proceedings of the National Academy of Sciences, 110:39 15758-15763.

Daley et al. (2005) "Rejoining of DNA Double-Strand Breaks as a Function of Overhang Length", Molecular and cellular Biology 25:3 896-906.

Dekker et al. (1960) "Nucleic Acids Selected Topics Related to their Enzymology and Chemistry", Review of Biochemistry 29: 453-474.

Didenko et al. (1998) "Biotin-Labeled Hairpin Oligonucleotides; Probes to Detect Double-Strand Breaks in DNA in Apoptotic Cells", American Journal of Pathology 152:4 897-902.

Didenko et al. (2003) "Early Necrotic DNA Degradation—Presence of Blunt-Ended DNA Breaks, 3' and 5' Overhangs in Apoptosis, but only 5' Overhangs in Early Necrosis", American Journal of Pathology 162:5 1571-1578.

Didenko et al. (2011) "In Situ Labeling of DNA Breaks and Apoptosis by T7 DNA Polymerase", Methods in Molecular Biology 682: 37-48.

Didenko et al. (1996) "Presence of Double-strand Breaks with Single-base 3' Overhangs in Cells Undergoing Apoptosis but Not Necrosis", The Journal of Cell Biology 135:5 1369-1376.

Diehl et al. (2008) "Circulating Mutant DNA to Assess Tumor Dynamics", Nature Medicine 14:9 985-990.

Dorsett et al.(2014) "HCoDES Reveals Chromosomal DNA End Structures with Single Nucleotide Resolution", Molecular Cell 56:6 808-818.

Enari (1998) "A Caspase-Activated DNase That Degrades DNA During Apoptosis, and Its Inhibitor ICAD", Nature 391:6662 43-50.

Ershova et al. (2017) "Circulating Cell-Free DNA Concentration and DNase I Activity of Peripheral Blood Plasma Change in Case of Pregnancy with Intrauterine Growth Restriction Compared to Normal Pregnancy", Biomedical Reports 7: 319-324.

Fan et al., (2008) "Noninvasive Diagnosis of Fetal Aneuploidy by Shotgun Sequencing DNA from Maternal Blood", Proceedings of the National Academy of Sciences of the United States of America 105:42 16266-16271.

Fischer et al. (2007) "DNase1L2 Degrades Nuclear DNA during Corneocyte Formation", Journal of Investigative Dermatology 127: 24-30.

Fischer et al. (2011) "Essential Role of the Keratinocyte-Specific Endonuclease DNase1L2 in the Removal of Nuclear DNA from Hair and Nails", Journal of Investigative Dermatology 131:6 1208-1215.

Frock et al. (2015) "Genome-Wide Detection of DNA Double-Stranded Breaks Induced by Engineered Nucleases", Nature Biotechnology 33: 179-186.

Gansauge et. al. (2017) "Single-stranded DNA library preparation from highly degraded DNA using T4 DNA ligase" Nucleic Acids Res. 45(10):e79:1-10.

International Preliminary Report on Patentability mailed Jan. 24, 2019 in International Patent Application No. PCT/US2017/041974, filed on Jul. 13, 2017, 8 pages.

(56) References Cited

OTHER PUBLICATIONS

International Preliminary Report on Patentability mailed on Oct. 14, 2021 in International Application Number PCT/US2020/026421, filed on Apr. 2, 2020, 8 pages.

International Preliminary Report on Patentability Received dated Dec. 17, 2020 in International Patent Application No. PCT/US2019/035617, filed on Jun. 5, 2019 and published as WO 2019/236726 on Dec. 12, 2019, 8 pages.

International Preliminary Report on Patentability Received dated Jul. 23, 2020 in PCT Patent Application No. PCT/US2019/013210, filed on Jan. 11, 2019 and published as WO 2019/140201 on Jul. 18, 2019, 8 pages.

International Search Report and Written Opinion mailed on May 13, 2019 in International Patent Application No. PCT/US2019/013210, filed on Jan. 11, 2019, 11 pages.

International Search Report and Written Opinion mailed on Oct. 12, 2017 in International Patent Application No. PCT/US2017/041974, filed on Jul. 13, 2017, 11 pages.

International Search Report and Written Opinion mailed on Sep. 13, 2019 in International Patent Application No. PCT/US2019/035617, filed on Jun. 5, 2019 and published as WO 2019/236726 on Dec. 12, 2019, 11 pages.

International Search Report and Written Opinion Received dated Jul. 30, 2020 in PCT Application No. PCT/US2020/026421, filed on Apr. 2, 2020, 12 pages.

International Search Report and Written Opinion Received dated Oct. 19, 2021 in PCT Application No. PCT/US2021/038609, filed on Jun. 23, 2021, 13 pages.

Office Action dated Jun. 28, 2021 in U.S. Appl. No. 16/316,268, filed Jan. 8, 2019, 15 pages.

Office Action dated Sep. 1, 2021 in U.S. Appl. No. 16/961,113, filed Jul. 9, 2020 and published as US-2021-0054366 on Feb. 25, 2021, 13 pages.

Gansauge et al. (2017) "Single-stranded DNA library preparation from highly degraded DNA using T4 DNA ligase" Nucleic Acids Research, 45(10):e79.

Genomes Project (2015) "A Global Reference for Human Genetic Variation", The 1000 Genomes Project Consortium, Nature 526: 68-74.

Gill et al. (2015) "Genotyping and Interpretation of STR-DNA: Low-Template, Mixtures and Database Matches—Twenty Years of Research and Development", Forensic Science International: Genetics 18: 100-117.

Goodwin et al. (2016) "Coming of Age: Ten Years of Next-Generation Sequencing Technologies", Nature Reviews Genetics 17: 333-351.

Green et al. (2008) "A Complete Neandertal Mitochondrial Genome Sequence Determined by High-Throughput Sequencing", Cell 134:3 416-426.

Green et al. (2010) "A Draft Sequence of the Neandertal Genome" Science, 328(5979):710-722.

Green et al. (2009) "The Neandertal Genome and Ancient DNA Authenticity", The EMBO Journal, 2009, 28:2494-2502.

Halazonetis et al. (2008) "An Oncogene-Induced DNA Damage Model for Cancer Development", Science 319: 1352-1355.

Harkins et al. (2017) "A New Method for Assessing Postmortem DNA Damage from Ancient Remains", The 86th Annual Meeting of the American Association of Physical Anthropologists, Abstract, 1 page.

Harkins et al. (2020) "A Novel NGS Library Preparation Method to Characterize Native Termini of Fragmented DNA", Nucleic Acids Research 48:8 13 pages.

Hashimoto et al. (2005) "Analysis of Telomeric Single-Strand Overhang Length in Human Endometrial Cancers", FEBS Letters 579: 2959-2964.

Homer et al. (2009) "BFAST: An Alignment Tool for Large Scale Genome Resequencing", PLoS One 4:11 e7767 12 pages.

Jobling et al. (2004) "Encoded Evidence: DNA in Forensic Analysis", Nature Reviews Genetics 5:10 739-751.

Kang et al. (2016) "Comparative Analysis of Circulating Tumor DNA Stability in K3EDTA, Streck and CellSave Blood Collection Tubes", Clinical Biochemistry 30 pages.

Karlin et al. (1993) "Applications and Statistics for Multiple High-Scoring Segments in Molecular Sequences", Proceedings of the National Academy of Sciences 90: 5873-5877.

Kayser et al. (2011) "Improving Human Forensics Through Advances in Genetics, Genomics and Molecular Biology", Nature Reviews Genetics 12:3 179-192.

Kent et al. (2002) "The Human Genome Browser at UCSC", Genome Research 12: 996-1006.

Kircher (2012) "Analysis of High-Throughput Ancient DNA Sequencing Data", Methods in Molecular Biology, Chapter 23, 840: 197-228.

Kivisild (2015) "Maternal Ancestry and Population History from Whole Mitochondrial Genomes", Investigative Genetics 6:3 10 pages.

Knierim et al. (2011) "Systematic Comparison of Three Methods for Fragmentation of Long-Range PCR Products for Next Generation Sequencing", PLoS One, 6:11 6 pages.

Koohy et al. (2013) "Chromatin Accessibility Data Sets Show Bias Due to Sequence Specificity of the DNase I Enzyme", PLoS One 8:7 9 pages.

Krings et al. (1997) "Neandertal DNA Sequences and the Origin of Modern Humans", Cell 90: 19-30.

Lahiri et al. (1993) "DNA Isolation by a Rapid Method from Human Blood Samples: Effects of MgCl2, EDTA, Storage Time, and Temperature on DNA Yield and Quality", Biochemical Genetics 31:718 321-328.

Langmead et al. (2009) "Ultrafast and Memory-Efficient Alignment of Short DNA Sequences to the Human Genome", Genome Biology, Article R25 10:3 10 pages.

Li et al. (2013) "Aligning Sequence Reads, Clone Sequences and Assembly Contigs with BWA-MEM", arXiv:1303 3 pages.

Li et al. (2009) "Fast and Accurate Short Read Alignment with Burrows-Wheeler Transform", Bioinformatics, 25:14 1754-1760.

Li et al. (2009) "SOAP2: An Improved Ultrafast Tool for Short Read Alignment", Bioinformatics, 25:15 1966-1967.

Li et al. (2009) "The Sequence Alignment/Map format and SAMtools", Bioinformatics 25:16 2078-2079.

Lieber et al. (2003) "Mechanism and Regulation of Human Non-Homologous DNA End-Joining", Nature Reviews Molecular Cell Biology vol. 4: 712-720.

Metzker (2010) "Sequencing Technologies—The Next Generation", Nature Review Genetics, 11: 31-46.

Meyer et al. (2010) "Illumina Sequencing Library Preparation for Highly Multiplexed Target Capture and Sequencing", Cold Spring Harbor Protocols 2010:6 20 pages.

Miller et al. (2008) "Sequencing the nuclear genome of the extinct woolly mammoth" Nature, 456(7220):387-390.

Monson-Miller et al. (2012) "Reference Genome-Independent Assessment of Mutation Density Using Restriction Enzyme-Phased Sequencing", BMC Genomics 13:72 15 pages.

Morey et al. (2013) "A Glimpse into Past, Present, and Future DNA Sequencing", Molecular Genetics and Metabolism 110:1-2 3-24.

Mukae et al. (1998) "Molecular Cloning and Characterization of Human Caspase-Activated DNase", Proceedings of the National Academy of Sciences 95: 9123-9128.

Mulero et al. (2008) "Development and Validation of the AmpFISTR MiniFiler PCR Amplification Kit: A MiniSTR Multiplex for the Analysis of Degraded And/or PCR Inhibited DNA", Journal of Forensic Sciences 53:4 838-852.

Oefner et al. (1996) "Efficient Random Subcloning of DNA Sheared in a Recirculating Point-Sink Flow System", Nucleic Acids Research 24:20 3879-3886.

Parkinson et al. (2012) "Preparation of High-Quality Next-Generation Sequencing Libraries from Picogram Quantities of Target DNA", Genome Research 22: 125-133.

Patel et al. (2000) "Evaluation of Serum Alkaline DNase Activity in Treatment Monitoring of Head and Neck Cancer Patients", Tumor Biology 21: 82-89.

Poinar et al. (2006) "Metagenomics to Paleogenomics: Large-Scale Sequencing of Mammoth DNA" Science, 311(5759):392-394.

(56) References Cited

OTHER PUBLICATIONS

Poptsova et al. (2014) "Non-Random DNA Fragmentation in Next-Generation Sequencing", Scientific Reports 4:4532 6 pages.

Prufer et al. (2010) "Computational Challenges in the Analysis of Ancient DNA", Genome Biology 11:R47 15 pages.

Raine et al. (2017) "SPlinted Ligation Adapter Tagging (SPLAT), a novel library preparation method for whole genome bisulphite sequencing" Nucleic Acid Res., 45(6):e36.

Rasmussen et al. (2010) "Ancient human genome sequence of an extinct Palaeo-Eskimo" Nature, 463(7282):757-762.

Reuter et al. (2015) "High-Throughput Sequencing Technologies", Molecular Cell 58: 586-597.

Rivals et al. (2009) "MPSCAN: Fast Localisation of Multiple Reads in Genomes", WABI 2009: Algorithms in Bioinformatics, LNBI 5724: 246-260.

Rizk et al. (2010) "GASSST: Global Alignment Short Sequence Search Tool", Bioinformatics 26:20 2534-2540.

Rushizky et al. (1960) "A Map of the Products Resulting from the Action of Micrococcal Nuclease on Thymus Deoxyribonucleic Acid and Its Use as a Guide to Specificity", Biochemical and Biophysical Research Communications 2:3 153-158.

Sabo et al. (2006) "Genome-Scale Mapping of DNase I Sensitivity in Vivo Using Tiling DNA Microarrays", Nature Methods 3:7 511-518.

Schweizer et al. (2016) "Targeted Capture and Resequencing of 1040 Genes Reveal Environmentally Driven Functional Variation in Grey Wolves", Molecular Ecology 25: 357-379.

Shapiro et al. (2014) "A Paleogenomic Perspective on Evolution and Gene Function: New Insights from Ancient DNA", Science 343: 8 pages.

Shinozuka et al. (2015) "A Simple Method for Semi-Random DNA Amplicon Fragmentation Using the Methylation-Dependent Restriction Enzyme MspJI", BMC Biotechnology 15:25 13 pages.

Shiroguchi et al. (2012) "Digital RNA Sequencing Minimizes Sequence-Dependent Bias and Amplification Noise with Optimized Single-Molecule Barcodes", Proceedings of the National Academy of Sciences 109:4 1347-1352.

Singh et al. (1988) "A Simple Technique for Quantitation of Low-Levels of DNA Damage in Individual Cells", Experimental Cell Research 175: 184-191.

Snyder et al. (2016) "Cell-free DNA Comprises an In Vivo Nucleosome Footprint that Informs Its Tissues-Of-Origin", Cell 164:1-2 57-68.

Sosic et al. (2017) "Edlib: A C/C++ Library for Fast, Exact Sequence Alignment Using Edit Distance", Bioinformatics 33:9 1394-1395.

SRSLYTM: A Directional NGS Library Preparation for the Analysis of Cell-Free DNA, Liquid Biopsy Summit, Abstract Only, 2019, 1 page.

Stiller et al. (2006) "Patterns of nucleotide misincorporations during enzymatic amplification and direct large-scale sequencing of ancient DNA" Proc. Natl. Acad. Sci., 103(37):13578-13584.

Sulkowski et al. (1962) "Mechanism of Action of Micrococcal Nuclease on Deoxyribonucleic Acid", Journal of Biological Chemistry 237:8 2620-2625.

Szabo et al. (2012) "In Situ Labeling of DNA Reveals Interindividual Variation in Nuclear DNA Breakdown in Hair and May Be Useful to Predict Success of Forensic Genotyping of Hair", International Journal of Legal Medicine 126: 63-70.

Tamkovich et al. (2006) "Circulating DNA and DNase Activity in Human Blood", Annals of the New York Academy of Sciences 1075: 191-196.

Tamkovich et al. (2016) "Features of Circulating DNA Fragmentation in Blood of Healthy Females and Breast Cancer Patients", Advances in Experimental Medicine and Biology 924: 47-51.

Thalmann et al. (2013) "Complete Mitochondrial Genomes of Ancient Canids Suggest a European Origin of Domestic Dogs", Science 342:871-874.

Troll et al. (2019) "A Ligation-Based Single-Stranded Library Preparation Method to Analyze Cell-Free DNA and Synthetic Oligos", BMC genomics 20:1023 14 pages.

Troll et al. (2019) "SRSLY: A Single-Stranded Approach to NGS Library Preparation for Analyses of Cell-Free DNA Fragments", Abstract Only 1 page.

Tsai et al. (2015) "GUIDE-Seq Enables Genome-Wide Profiling of Off-Target Cleavage by CRISPR-Cas Nucleases", Nature Biotechnology 33:2 187-197.

Van Oorschot et al. (2010) "Forensic Trace DNA: A Review", Investigative Genetics 1:14 17 pages.

Van Oven et al. (2008) "Updated Comprehensive Phylogenetic Tree of Global Human Mitochondrial DNA Variation", Human Mutation 30:2 E386-394.

Vohr et al. (2015) "A Method for Positive Forensic Identification of Samples from Extremely Low-Coverage Sequence Data", BMC Genomics 16:1034 11 pages.

Wan et al. (2017) "Liquid Biopsies Come of Age: Towards Implementation of Circulating Tumour DNA", Nature Reviews Cancer 17: 48 pages.

Widlak et al. (2000) "Cleavage Preferences of the Apoptotic Endonuclease DFF40 (Caspaseactivated DNase or Nuclease) on Naked DNA and Chromatin Substrates", The Journal of Biological Chemistry 275:11 8226-8232.

Wong et al. (2013) "Optimizing Blood Collection, Transport and Storage Conditions for cell free DNA Increases Access to Prenatal Diagnostic Testing", Clinical Biochemistry 46:1099-1104.

Wu and Lambowitz (2017) "Facile single-stranded DNA sequencing of human plasma DNA via thermostable group II intron reverse transcriptase template switching" Scientific Reports, 7:8421.

Wu et al. (2018) "SALP, a new single-stranded DNA library preparation method especially useful for the high-throughput characterization of chromatin openness states" BMC Genomics, 19:143.

Wu et al. (2019) "Decoding genetic and epigenetic information embedded in cell free DNA with adapted SALP-seq" Int. J. Cancer, 00:13 pages.

Wylie (1980) "Glucocorticoid-Induced Thymocyte Apoptosis Is Associated with Endogenous Endonuclease Activation", Nature 284: 555-556.

Yan et al. (2017) "BLISS Is a Versatile and Quantitative Method for Genome-Wide Profiling of DNA Double-Strand Breaks", Nature Communications 8:15058 9 pages.

Zhao et al. (2008) "Quantitative Telomeric Overhang Determination Using a Double-Strand Specific Nuclease", Nucleic Acids Research 36:3 5 pages.

Imamura, Takuya: "DNA Methylation Analysis by Bisulfite Sequencing", National Institute for Basic Biology, Division of Behavioral Control Research, 2004, No. 113, pp. 113_25-113_29 [https://doi.org/10.5983/nl2001jsce.2004.113_25].

Green et al., "Forensic Identification from Mixed and Minute Samples", Funding Opportunity No. CFDA No. 16.560, University of California, Santa Cruz, 2017, 22 pages.

Office Action received for U.S. Appl. No. 17/440,386, mailed on Apr. 8, 2025, 31 pages.

Prediger, Ellen "Oligo Modifications that Block Nuclease Degradation Integrated DNA Technologies, Retrieved from the Internet: URL:https://www.idtdna.com/pages/education/decoded/article/modification-highlightmodifications-that-block-nuclease-degradation", Date Published Jan. 14, 2014, 3 pages.

Vohr et al. (2017) "A Phylogenetic Approach for Haplotype Analysis of Sequence Data from Complex Mitochondrial Mixtures", Forensic Science International: Genetics 30: 93-105.

Agarwal, et al., "Sequencing of first-strand cDNA library reveals full-length transcriptomes", Nature Communications, vol. 6, No. 1, Article 6002, Jan. 21, 2015, 12 pages.

Final Office Action received for U.S. Appl. No. 18/299,553, mailed on Jun. 6, 2025, 10 pages.

International Preliminary Report on Patentability received for PCT Application No. PCT/US2023/032110, mailed on Mar. 20, 2025, 8 pages.

Non-Final Office Action received for U.S. Appl. No. 17/440,386, mailed on Apr. 8, 2025, 32 pages.

Stiller et al., Single-strand DNA library preparation improves sequencing of formalin-fixed and paraffin-embedded (FFPE) cancer DNA, Oncotarget, 7(37);59115-59128, Jul. 24, 2016.

(56) References Cited

OTHER PUBLICATIONS

Aucamp et al., The diverse origins of circulating cell-free DNA in the human body: a critical re-evaluation of the literature, Biological reviews, 93(3):1649-1683, 2018.

Head et al., Library construction for next-generation sequencing: Overviews and challenges, BioTechniques, 56(2); Apr. 3, 2018.

Kershaw et al, Splint Ligation of RNA with T4 DNA Ligase, Methods in Molecular Biology, 941:257-269, 2012.

Gansauge et al., A Method for Single-Stranded Ancient DNA Library Preparation, Methods in Molecular Biology, 1963:75-83, 2019.

Burnham et al., Single-stranded DNA library preparation uncovers the origin and diversity of ultrashort cell-free DNA in plasma, Scientific reports, 6:27859, Jun. 14, 2016.

Peterson, et al., "Double Digest RADseq: An Inexpensive Method for De Novo SNP Discovery and Genotyping in Model and Non-Model Species", PLOS One, vol. 7, No. 5, pp. 1-11.

Schweyen, et al., "Detection and Removal of PCR Duplicates in Population Genomic ddRAD Studies by Addition of a Degenerate Base Region (DBR) in Sequencing Adapters", The Biological Bulletin, vol. 227, Oct. 2014, pp. 146-160.

Notice of Allowance received for U.S. Appl. No. 18/299,553, mailed on Oct. 9, 2025, 8 pages.

Non-Final Office Action received for U.S. Appl. No. 18/011,271, mailed on Nov. 28, 2025, 23 pages.

Communication of a Notice of Opposition received for EP Patent Application No. 20722098.9, mailed on Sep. 24, 2025, 41 pages.

Final Office Action received for U.S. Appl. No. 17/440,386, mailed on Oct. 1, 2025, 37 pages.

English Translation of Japanese Opposition Documents for Japanese Patent No. 7651470, dated Dec. 23, 2025 51 pages).

Chen et al., A cost-effective method for Illumina small RNA-Seq library preparation using T4 RNA ligase 1 adenylated adapters, Plant Methods, 8(1):41, 2012.

Brief Communication received for European Application No. 207220989, mailed on May 8, 2026, 37 pages.

Final Office Action received for U.S. Appl. No. 17/440,386, mailed on May 5, 2026, 39 pages.

Final Office Action received for U.S. Appl. No. 18/011,271, mailed on May 14, 2026, 28 pages.

Smith (2015) "Unique Molecular Identifiers—the problem, the solution and the proof" Retrieved from: https://cgatoxford.wordpress.com/2015/08/14/unique-molecular-identifiers-the-problem-the-solution-and-the-proof, 10 pages.

* cited by examiner

Degraded DNA - 0.7pmol - 35bp Avg Size

Modern DNA - 1pmol - 250bp avg length

SEQUENCE LISTING

```
Sequence total quantity: 4
SEQ ID NO: 1              moltype = DNA   length = 33
FEATURE                  Location/Qualifiers
misc_feature             1..33
                         note = Synthetic sequence
source                   1..33
                         mol_type = other DNA
                         organism = synthetic construct
SEQUENCE: 1
acactctttc cctacacgac gctcttccga tct                                    33

SEQ ID NO: 2              moltype = DNA   length = 40
FEATURE                  Location/Qualifiers
misc_feature             1..40
                         note = Synthetic sequence
misc_feature             1..7
                         note = n is a, c, g, or t
source                   1..40
                         mol_type = other DNA
                         organism = synthetic construct
SEQUENCE: 2
nnnnnnnaga tcggaagagc gtcgtgtagg gaaagagtgt                             40

SEQ ID NO: 3              moltype = DNA   length = 34
FEATURE                  Location/Qualifiers
misc_feature             1..34
                         note = Synthetic sequence
source                   1..34
                         mol_type = other DNA
                         organism = synthetic construct
SEQUENCE: 3
agatcggaag agcacacgtc tgaactccag tcac                                   34

SEQ ID NO: 4              moltype = DNA   length = 41
FEATURE                  Location/Qualifiers
misc_feature             1..41
                         note = Synthetic sequence
misc_feature             35..41
                         note = n is a, c, g, or t
source                   1..41
                         mol_type = other DNA
                         organism = synthetic construct
SEQUENCE: 4
gtgactggag ttcagacgtg tgctcttccg atctnnnnnn n                           41
```

METHODS OF PRODUCING NUCLEIC ACID LIBRARIES AND COMPOSITIONS AND KITS FOR PRACTICING SAME

CROSS-REFERENCE TO RELATED APPLICATIONS

This application is a divisional of U.S. patent application Ser. No. 17/058,066, filed on Nov. 23, 2020; which is a national phase of PCT/US2019/035617 filed on Jun. 5, 2019; which claims the benefit of U.S. Provisional Patent Application No. 62/681,524, filed Jun. 6, 2018, which application is incorporated herein by reference in its entirety.

INCORPORATION BY REFERENCE OF SEQUENCE LISTING PROVIDED AS A SEQUENCE LISTING XML FILE

A Sequence Listing is provided herewith as a Sequence Listing XML, UCSC-376DIV_SEQ_LIST, created on Apr. 12, 2023 and having a size of 7,022 bytes. The contents of the Sequence Listing XML are incorporated herein by reference in their entirety.

INTRODUCTION

Nucleic acid sequencing has become an increasingly important area of genetic research, with uses in diagnostic and other applications. In general, nucleic acid sequencing consists of determining the order of nucleotides for a nucleic acid such as a fragment of RNA or DNA. Relatively short sequences are typically analyzed, and the resulting sequence information may be used in various bioinformatics methods to align fragments against a reference sequence or to logically fit fragments together so as to reliably determine the sequence of much more extensive lengths of genetic material from which the fragments were derived. Automated, computer-based examination of characteristic fragments have been developed, and have been used more recently in genome mapping, analysis of genetic variation between individuals, identification of genes and their function, and the like.

Several methods employed for high throughput DNA sequencing rely on a universal amplification reaction, whereby a DNA sample is randomly fragmented, then treated such that the ends of the different fragments all contain the same DNA sequence. Fragments with universal ends can be amplified in a single reaction with a single pair of amplification primers. The addition of universal priming sequences onto the ends of targets to be amplified by PCR can be achieved by a variety of methods. For example, a universal primer with a universal sequence at its 5' end and a degenerate sequence at its 3' end can be used to amplify fragments randomly from a complex target sequence or a complex mixture of target sequences. The degenerate 3' portion of the primer anneals at random positions on DNA and can be extended to generate a copy of the target that has the universal sequence at its 5' end.

Alternatively, adapters that contain universal priming sequences can be ligated onto the ends of the target sequences. One or more adapters may be used in a ligation reaction with target sequences. Drawbacks associated with current methods for preparing nucleic acid sequencing libraries via ligation of one or more adapter sequences for universal amplification are the time and expense required by such methods.

SUMMARY

Provided are methods of producing nucleic acid libraries. The methods include combining single-stranded nucleic acid binding protein-bound single-stranded nucleic acid (SSB-bound ssNA), an adapter oligonucleotide, and a splint oligonucleotide, to form complexes including the splint oligonucleotide hybridized to a terminal region of the SSB-bound ssNA and to the adapter oligonucleotide. An end of the first adapter oligonucleotide is adjacent to an end of the first terminal region of the SSB-bound ssNA, and the methods may further include covalently linking the adjacent ends. Also provided are compositions and kits that find use, e.g., in practicing the methods of the present disclosure.

DETAILED DESCRIPTION

Figure 1:
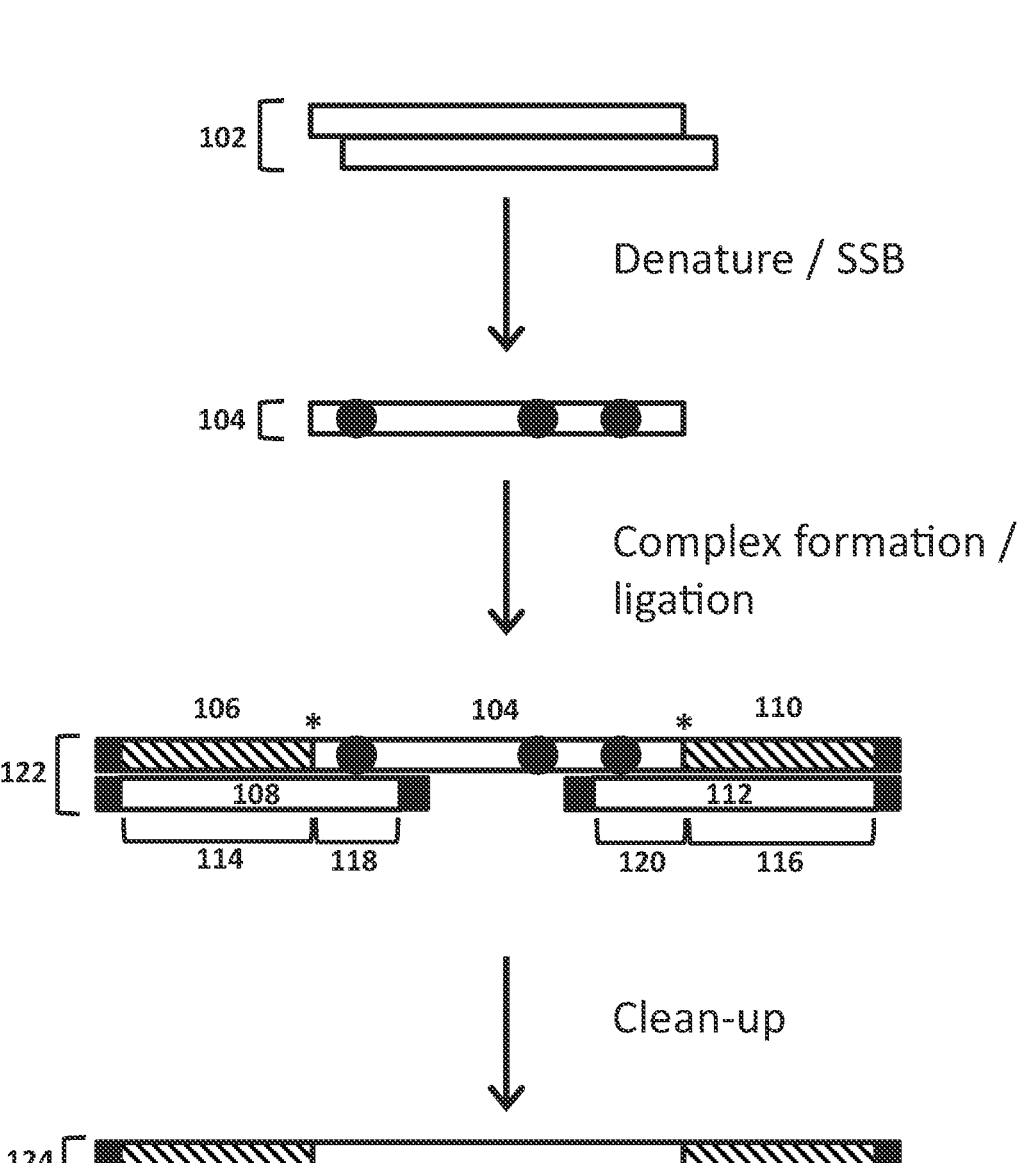
FIG. 1. Schematic illustration of a method of producing a nucleic acid library according to one embodiment of the present disclosure.

Provided are methods of producing nucleic acid libraries. The methods include combining single-stranded nucleic acid binding protein-bound single-stranded nucleic acid (SSB-bound ssNA), an adapter oligonucleotide, and a splint oligonucleotide, to form complexes including the splint oligonucleotide hybridized to a terminal region of the SSB-bound ssNA and to the adapter oligonucleotide. An end of the first adapter oligonucleotide is adjacent to an end of the first terminal region of the SSB-bound ssNA, and the methods may further include covalently linking the adjacent ends. Also provided are compositions and kits that find use, e.g., in practicing the methods of the present disclosure.

Before the methods, compositions and kits of the present disclosure are described in greater detail, it is to be understood that the methods, compositions and kits are not limited to particular embodiments described, as such may, of course, vary. It is also to be understood that the terminology used herein is for the purpose of describing particular embodiments only, and is not intended to be limiting, since the scope of the methods, compositions and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, compositions and kits. The upper and lower limits of these smaller ranges may independently be included in the smaller ranges and are also encompassed within the methods, compositions and kits, subject to any specifically excluded limit in the stated range. Where the stated range includes one or both of the limits, ranges excluding either or both of those included limits are also included in the methods, compositions and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, compositions and kits belong. Although any methods, compositions and kits similar or equivalent to those described herein can also be used in the practice or testing of the methods, compositions and kits, representative illustrative methods, compositions and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, compositions and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, compositions and kits, which are, for clarity, described in the context of separate embodiments, may also be provided in combination in a single embodiment. Conversely, various features of the methods, compositions and kits, which are, for brevity, described in the context of a single embodiment, may also be provided separately or in any suitable subcombination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods, compositions and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

As summarized above, the present disclosure provides methods of producing nucleic acid libraries. The methods include contacting single-stranded nucleic acid (ssNA) with single-stranded nucleic acid binding protein (SSB) to produce SSB-bound ssNA. The methods further include combining the SSB-bound ssNA, a first adapter oligonucleotide, and a first splint oligonucleotide including an SSB-bound ssNA hybridization region and a first adapter oligonucleotide hybridization region. The combining results in the formation of complexes including the first splint oligonucleotide hybridized to a terminal region of the SSB-bound ssNA via the SSB-bound ssNA hybridization region, and the first splint oligonucleotide hybridized to the first adapter oligonucleotide via the first adapter oligonucleotide hybridization region, such that an end of the first adapter oligonucleotide is adjacent to an end of the first terminal region of the SSB-bound ssNA. In some embodiments the combining further includes combining the SSB-bound ssNA, a second adapter oligonucleotide, and a second splint oligonucleotide including an SSB-bound ssNA hybridization region and a second adapter oligonucleotide hybridization region, where the formed complexes further include the second splint oligonucleotide hybridized via the SSB-bound ssNA hybridization region to the terminal region of the SSB-bound ssNA opposite the terminal region hybridized to the first splint oligonucleotide, and the second splint oligonucleotide hybridized to the second adapter oligonucleotide via the second adapter oligonucleotide hybridization region, such that an end of the second adapter oligonucleotide is adjacent to the end of the SSB-bound ssNA opposite the end adjacent to the first adapter oligonucleotide.

An example embodiment in which a second adapter oligonucleotide and a second splint oligonucleotide are employed is schematically illustrated in FIG. 1. In this example, ssNA is produced from dsNA (e.g., ssDNA produced from dsDNA) by denaturing the dsNA. Shown at the top of FIG. 1 is dsNA 102. Upon denaturation of the dsNA 102, the resulting ssNA is contacted with single-stranded nucleic acid binding protein (SSB) to produce SSB-bound ssNA. Shown in FIG. 1 is SSB-bound ssNA 104 derived from a strand of dsNA 102. In this example, ssNA 104 is combined with a first adapter oligonucleotide 106 hybridized to a first splint oligonucleotide 108, and a second adapter oligonucleotide 110 hybridized to a second splint oligonucleotide 112. Hybridization of the first splint oligonucleotide 108 to the first adapter oligonucleotide 106 is via a first adapter oligonucleotide hybridization region 114 of the first splint oligonucleotide 108. Hybridization of the second splint oligonucleotide 112 to the second adapter oligonucleotide 110 is via a second adapter oligonucleotide hybridization region 116 of the second splint oligonucleotide 112. The hybridization of the first splint oligonucleotide 108 and the second splint oligonucleotide 112 with the SSB-bound NA 104, the first adapter region 106, and the second adapter region 110 forms a complex 122. Hybridization of the first splint oligonucleotide 108 to a 5' terminal region of SSB-bound ssNA 104 is via a first SSB-bound ssNA hybridization region 118 of the first splint oligonucleotide 108. Hybridization of the second splint oligonucleotide 112 to a 3' terminal region of the SSB-bound ssNA 104 is via a second SSB-bound ssNA hybridization region 120 of the second splint oligonucleotide 112. The splint oligonucleotides are designed such that when the SSB-bound ssNA hybridization regions of the splint oligonucleotides are hybridized to their respective terminal regions of the SSB-bound ssNA, an end of the adapter oligonucleotide is adjacent to an end of the SSB-bound ssNA. The locations of adjacent ends are indicated by asterisks. These adjacent ends may be covalently linked (e.g., by enzymatic ligation) to produce adapted ssNA (e.g., adapted ssNA 124 shown in FIG. 1) which may then be used in a downstream application of interest (e.g., PCR amplification, next-generation sequencing, and/or the like) facilitated by one or more sequences in the adapter portion of the adapted ssNA. As shown in FIG. 1, upon covalent linkage of the adjacent ends, an optional clean-up step may be performed to separate the adapted ssNA from one or more reagents or components of the formed complexes, e.g., enzyme used for the covalent linkage, splint oligonucleotides, SSB, and/or the like. Suitable approaches for such a clean-up step include, but are not limited to, solid phase reversible immobilization (SPRI—e.g., using magnetic beads) and nucleic acid column purification. In the example shown in FIG. 1, a blocking modification is present at each end of the splint oligonucleotides (black rectangles), and a blocking modification is further present at the end of each adapter oligonucleotide which is not adjacent to the SSB-bound ssNA (black rectangles). The blocking modifications prevent ligation of oligonucleotides and ssNA to those ends.

As summarized above, drawbacks associated with current methods for preparing nucleic acid sequencing libraries via ligation of one or more adapter sequences include the time and expense required by such methods. The methods of the present disclosure constitute an improvement of current state-of-the-art approaches to single-stranded library preparation, such as the approach (designated "ssDNA2.0") described by Gansauge et al. (2017) *Nucleic Acids Research* 45(10):e79, where the present methods were surprisingly found to be more efficient, require less time, and reduce costs. Aspects of the methods of the present disclosure will now be described in further detail.

The subject methods include contacting single-stranded nucleic acid (ssNA) with single-stranded nucleic acid binding protein (SSB) to produce SSB-bound ssNA. By "single-stranded nucleic acid" or "ssNA" is meant a collection of polynucleotides which are single-stranded (that is, not hybridized intermolecularly or intramolecularly) over 70% or more of their length. In some embodiments, the ssNA is single-stranded over 75% or more, 80% or more, 85% or more, 90% or more, 95% or more, or 99% or more, of the length of the polynucleotides. In certain aspects, the ssNA is single-stranded over the entire length of the polynucleotides.

The ssNA may be (or be prepared from) any nucleic acid sample of interest, including but not limited to, a nucleic acid sample isolated from a single cell, a plurality of cells (e.g., cultured cells), a tissue, an organ, or an organism (e.g., bacteria, yeast, or the like). Exemplary sample types include but are not limited to blood, serum, saliva, sputum, urine, feces, vomitus, mucus, hair, nail (e.g., fingernail, toenail), swabs (e.g., cheek swabs, throat swabs, vaginal swabs), biopsied tissue (e.g., punch biopsies, fine-needle biopsies, fine-needle aspiration biopsies), cell culture, environmental samples (e.g., water, soil, air, surfaces, touch DNA), and metagenomic samples. In certain aspects, the nucleic acid sample is isolated from a single cell, collection of cells, tissue, organ, and/or the like of an animal. In some cases, the nucleic acid sample comprises cell-free nucleic acids (e.g., cell-free DNA (cfDNA)), such as but not limited to fetal cell free nucleic acids (e.g., cell-free fetal DNA (cffDNA)) or circulating tumor nucleic acids (e.g., circulating tumor DNA (ctDNA)). In some embodiments, the animal is a mammal (e.g., a mammal from the genus *Homo*, a rodent (e.g., a mouse or rat), a dog, a cat, a horse, a cow, or any other mammal of interest). In other aspects, the nucleic acid sample is isolated/obtained from a source other than a mammal, such as bacteria, yeast, insects (e.g., *Drosophila*), amphibians (e.g., frogs (e.g., *Xenopus*)), viruses, plants, or any other non-mammalian nucleic acid sample source.

In some embodiments, the ssNA is from a degraded nucleic acid sample. As used herein, a "degraded nucleic acid sample" is a sample of DNA that has been fragmented by enzymatic, physical, chemical or other processes. Examples of degraded nucleic acid samples are the DNA fragments recovered from bone remains, hair, cell-free DNA from blood plasma, or environmental DNA recovered from soil or water. In certain aspects, when the ssNA is from a degraded nucleic acid sample, the ssNA is from an ancient nucleic acid sample. By "ancient nucleic acid sample" is meant nucleic acid fragments recovered from biological remains. A non-limiting example of an ancient nucleic acid sample of interest is a nucleic acid sample obtained (e.g., isolated) from an extinct organism or animal, e.g., an extinct mammal. In certain aspects, the extinct mammal is from the genus *Homo*. In some embodiments, the ssNA is from a forensic nucleic acid sample. As used herein, a "forensic nucleic acid sample" is a nucleic acid sample relating to (e.g., obtained during the course of) the investigation of a crime.

In certain aspects, the ssNA is from a tumor nucleic acid sample (that is, a nucleic acid sample isolated from a tumor). As used herein, "tumor" refers to all neoplastic cell growth and proliferation, whether malignant or benign, and all pre-cancerous and cancerous cells and tissues. The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, and the like.

In some embodiments, the ssNA is from a cell-free nucleic acid sample, e.g., cell-free DNA, cell-free RNA, or both. In certain aspects, the cell-free nucleic acids are obtained from a body fluid sample selected from the group consisting of: whole blood, blood plasma, blood serum, amniotic fluid, saliva, urine, pleural effusion, bronchial lavage, bronchial aspirates, breast milk, colostrum, tears, seminal fluid, peritoneal fluid, pleural effusion, and stool. In some embodiments, the cell-free nucleic acids are cell-free fetal DNAs. In certain aspects, the cell-free nucleic acids are circulating tumor DNAs. In some embodiments, the cell-free nucleic acids comprise infectious agent DNAs. In certain aspects, the cell-free nucleic acids comprise DNAs from a transplant.

In certain aspects, the ssNA is single-stranded deoxyribonucleic acid (ssDNA). ssDNA of interest includes, but is not limited to, ssDNA derived from double-stranded DNA (dsDNA). For example, the ssDNA may be derived from double-stranded DNA which is denatured (e.g., heat-denatured and/or chemically-denatured) to produce the ssDNA. In some embodiments, the methods include, prior to contacting the ssDNA with SSB, producing the ssDNA by denaturing the dsDNA.

When the ssNA is ssDNA derived from a dsDNA sample, the methods may further include, after formation of the complexes, rehybridizing the ssDNA (which now includes one or more adapters (e.g., sequencing adapters) at one or both ends) to produce dsDNA. If desired, the produced dsDNA may be sequenced. In some embodiments, the rehybridizing is carried out under sufficiently stringent hybridization conditions to produce dsDNAs that resemble the original dsDNAs from which the ssDNA was derived. The sufficiently stringent hybridization conditions may include a selected hybridization temperature, a selected salt concentration, and/or any other convenient hybridization parameters selected to produce dsDNAs that resemble the original dsDNAs from which the ssDNA was derived. One or both ends of at least a subset of such produced dsDNAs will resemble/replicate the ends (e.g., overhangs) of the original dsDNAs. Determining the end/overhang content (e.g., by sequencing) using the methods of the present disclosure may provide a variety of useful information regarding the nucleic acid sample from which the ssDNA was derived. For example, knowing the overhang content is of value in analyzing cell-free DNA (cfDNA), e.g., from blood plasma or another suitable source. It has been shown that cfDNA derives from a variety of sources including blood cells, fetal cells in pregnant women, tumor cells in individuals having cancer, from transplanted organ tissue in organ transplant recipients, etc. The overhang content provided by embodiments of the methods of the present disclosure can be used to classify sequencing reads, e.g., by source of origin for diagnostic purposes.

Moreover, the end/overhang content may be used to analyze mixed DNA from forensic samples. For example, DNA from semen, blood, or another source of interest may have end characteristics that are diagnostic for that source, and DNA sequences could be partitioned based on this information.

In addition, determining the overhang content in an ancient DNA sample (e.g., a sample from an extinct organism, plant, or animal) provides information useful in characterizing such samples and the organisms, plants, animals, etc. from which the sample is derived. For example, ancient DNA samples (e.g., a DNA sample from an extinct mammal) often include contaminating DNAs (e.g., contaminating bacterial DNA, or the like). In such cases, the DNA sequences of interest may be partitioned from the contaminating DNA sequences based on the types of overhangs detected, when such types of overhangs are associated with a particular source of DNA.

In certain embodiments, the methods of the present disclosure find use in determining the rate and position of base damage in DNA extracts (e.g., ancient DNA extracts), as a function of the length and type of overhang.

Accordingly, in some embodiments, provided are methods that include combining SSB-bound dsDNA-derived ssDNA with the adapter and splint oligonucleotides to form complexes including the SSB-bound dsDNA-derived ssDNA hybridized to the adapter and splint oligonucleotides as described herein, and subsequent to complex formation, rehybridizing the ssDNA to produce dsDNAs (that is, "adapted" dsDNAs which now include one or more adapters (e.g., sequencing adapters) at one or both ends) that resemble the original dsDNAs from which the ssDNA was derived. Such methods may further include sequencing the adapted dsDNAs. In certain aspects, the sequencing is to determine the end/overhang content of the dsDNAs from which the ssDNA was derived. In any embodiments of the methods of the present disclosure which involve sequencing, the methods may include sequencing a subsample of the adapted ssNAs in order to reduce the complexity during sequencing.

In some embodiments, the ssNA is single-stranded ribonucleic acid (ssRNA). RNAs of interest include, but are not limited to, messenger RNA (mRNA), microRNA (miRNA), small interfering RNA (siRNA), transacting small interfering RNA (ta-siRNA), natural small interfering RNA (nat-siRNA), ribosomal RNA (rRNA), transfer RNA (tRNA), small nucleolar RNA (snoRNA), small nuclear RNA (snRNA), long non-coding RNA (lncRNA), non-coding RNA (ncRNA), transfer-messenger RNA (tmRNA), precursor messenger RNA (pre-mRNA), small Cajal body-specific RNA (scaRNA), piwi-interacting RNA (piRNA), endoribonuclease-prepared siRNA (esiRNA), small temporal RNA (stRNA), signal recognition RNA, telomere RNA, ribozyme, or any combination of such RNA types or subtypes. In some embodiments, when the ssNA is ssRNA, the ssRNA is mRNA.

Approaches, reagents and kits for isolating, purifying and/or concentrating DNA and RNA from sources of interest are known in the art and commercially available. For example, kits for isolating DNA from a source of interest include the DNeasy®, RNeasy®, QIAamp®, QIAprep® and QIAquick® nucleic acid isolation/purification kits by Qiagen, Inc. (Germantown, Md); the DNAzol®, ChargeSwitch®, Purelink®, GeneCatcher® nucleic acid isolation/purification kits by Life Technologies, Inc. (Carlsbad, CA); the NucleoMag®, NucleoSpin®, and Nucleo-Bond® nucleic acid isolation/purification kits by Clontech Laboratories, Inc. (Mountain View, CA). In certain aspects, the nucleic acid is isolated from a fixed biological sample, e.g., formalin-fixed, paraffin-embedded (FFPE) tissue. Genomic DNA from FFPE tissue may be isolated using commercially available kits—such as the AllPrep® DNA/RNA FFPE kit by Qiagen, Inc. (Germantown, Md), the RecoverAll® Total Nucleic Acid Isolation kit for FFPE by Life Technologies, Inc. (Carlsbad, CA), and the Nucleo-Spin® FFPE kits by Clontech Laboratories, Inc. (Mountain View, CA).

When an organism, plant, animal, etc. from which the nucleic acid sample is obtained (e.g., isolated) is extinct, suitable strategies for recovering such nucleic acids are known and include, e.g., those described in Green et al. (2010) *Science* 328(5979):710-722; Poinar et al. (2006) *Science* 311(5759):392-394; Stiller et al. (2006) *Proc. Natl. Acad. Sci.* 103(37):13578-13584; Miller et al. (2008) *Nature* 456(7220):387-90; Rasmussen et al. (2010) *Nature* 463 (7282):757-762; and elsewhere.

As summarized above, the subject methods include contacting the ssNA with single-stranded nucleic acid binding protein (SSB) to produce SSB-bound ssNA. SSB binds in a cooperative manner to ssNA and does not bind well to double-stranded nucleic acid (dsNA). Upon binding ssDNA, SSB destabilizes helical duplexes. SSBs that may be employed when practicing the subject methods include prokaryotic SSB (e.g., bacterial or archaeal SSB) and eukaryotic SSB. Non-limiting examples of SSBs that may be employed when practicing the subject methods include *E. coli* SSB, *E. coli* RecA, Extreme Thermostable Single-Stranded DNA Binding Protein (ET SSB), *Thermus thermophilus* (Tth) RecA, T4 Gene 32 Protein, replication protein A (RPA—a eukaryotic SSB), and the like. ET SSB, Tth RecA, *E. coli* RecA, T4 Gene 32 Protein, as well buffers and detailed protocols for preparing SSB-bound ssNA using such SSBs are available from, e.g., New England Biolabs, Inc. (Ipswich, MA). The inventors have determined that, given equal molarity inputs, a greater input of SSB is beneficial for ssNAs with higher average fragment lengths. Detailed guidance regarding example approaches for contacting ssNA with SSB to produce SSB-bound ssNA is provided in the Experimental section below.

As summarized above, the subject methods include combining the SSB-bound ssNA, the adapter oligonucleotide, and the splint oligonucleotide that includes an SSB-bound ssNA hybridization region and a adapter oligonucleotide hybridization region, to form the complexes. As used herein, an "oligonucleotide" is a single-stranded multimer of nucleotides from 5 to 500 nucleotides, e.g., 5 to 100 nucleotides. Oligonucleotides may be synthetic or may be made enzymatically, and, in some embodiments, are 5 to 50 nucleotides in length. Oligonucleotides may contain ribonucleotide monomers (i.e., may be oligoribonucleotides or "RNA oligonucleotides"), deoxyribonucleotide monomers (i.e., may be oligodeoxyribonucleotides or "DNA oligonucleotides"), or a combination thereof. Oligonucleotides may be 10 to 20, 20 to 30, 30 to 40, 40 to 50, 50 to 60, 60 to 70, 70 to 80, 80 to 100, 100 to 150 or 150 to 200, or up to 500 nucleotides in length, for example.

An "adapter oligonucleotide" of the present disclosure is an oligonucleotide that includes an adapter or portion thereof. By "adapter" is meant a nucleotide sequence useful for one or more downstream applications (e.g., PCR amplification of the adapted ssNA or derivative thereof, sequencing of the adapted ssNA or derivative thereof, and/or the like). In certain aspects, the adapter or portion thereof present in the adapter oligonucleotide is a sequencing adapter. By "sequencing adapter" is meant one or more nucleic acid domains that include at least a portion of a nucleotide sequence (or complement thereof) utilized by a sequencing platform of interest, such as a sequencing platform provided by Illumina® (e.g., the HiSeq™, MiSeq™ and/or Genome Analyzer™ sequencing systems); Oxford Nanopore™ Technologies (e.g., the MinION™ sequencing system), Ion Torrent™ (e.g., the Ion PGM™ and/or Ion Proton™ sequencing systems); Pacific Biosciences (e.g., a Sequel or PacBio RS II sequencing system); Life Technologies™ (e.g., a SOLiD™ sequencing system); Roche (e.g., the 454 GS FLX+ and/or GS Junior sequencing systems); or any other sequencing platform of interest.

In certain aspects, the sequencing adapter is, or includes, a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a unique identifier (e.g., a barcode or other domain that uniquely identifies the 3' region of the oligonucleotide probe, the probe complement oligonucleotide, or both, and/or uniquely identifies the sample source of the rRNA being sequenced to enable sample multiplexing by marking every molecule from a given sample with a specific barcode or "tag"); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest, e.g., to determine expression levels based on the number of instances a unique tag is sequenced; a complement of any such domains; or any combination thereof. In certain aspects, a barcode domain (e.g., sample index tag) and a molecular identification domain (e.g., a molecular index tag) may be included in the same nucleic acid.

When the adapter oligonucleotide includes one or a portion of a sequencing adapter, one or more additional sequencing adapters and/or a remaining portion of the sequencing adapter may be added using a variety of approaches. For example, additional and/or remaining portions of sequencing adapters may be added by ligation, reverse transcription, PCR amplification, and/or the like. In the case of PCR, an amplification primer pair may be employed that includes a first amplification primer that includes a 3' hybridization region (e.g., for hybridizing to an adapter region of the adapter oligonucleotide) and a 5' region including an additional and/or remaining portion of a sequencing adapter, and a second amplification primer that includes a 3' hybridization region (e.g., for hybridizing to an adapter region of a second adapter oligonucleotide added to the opposite end of an ssNA molecule) and optionally a 5' region including an additional and/or remaining portion of a sequencing adapter.

A "splint oligonucleotide" of the present disclosure is an oligonucleotide that includes an SSB-bound ssNA hybridization region and an adapter oligonucleotide hybridization region. The SSB-bound ssNA hybridization region is a region (nucleotide sequence) that hybridizes to a terminal region of the SSB-bound ssNA. The adapter oligonucleotide hybridization region is a region (nucleotide sequence) that hybridizes to all or a portion of the adapter oligonucleotide. The splint oligonucleotide is designed for simultaneous hybridization to the SSB-bound ssNA and the adapter oligonucleotide such that, upon complex formation, an end of the adapter oligonucleotide is adjacent to an end of the terminal region of the SSB-bound ssNA.

The SSB-bound ssNA hybridization region of the splint oligonucleotide may have any suitable length and sequence. In some embodiments, the length of the SSB-bound ssNA hybridization region is 10 nucleotides or less. In certain aspects, the SSB-bound ssNA hybridization region is from 4 to 20 nucleotides in length, e.g., from 5 to 15, 5 to 10, 5 to 9, 5 to 8, or 5 to 7 (e.g., 6 or 7) nucleotides in length. In some embodiments, the SSB-bound ssNA hybridization region includes (e.g., consists of) a random nucleotide sequence, such that when a plurality of heterogeneous splint oligonucleotides having various random SSB-bound ssNA hybridization regions are employed, the collection is capable of acting as splint oligonucleotides for a heterogeneous population of SSB-bound ssNAs irrespective of the sequences of the terminal regions of the SSB-bound ssNAs.

Accordingly, in certain aspects, the methods include forming the complexes by combining the SSB-bound ssNA, an adapter oligonucleotide, and a plurality of heterogeneous splint oligonucleotides having various random SSB-bound ssNA hybridization regions capable of acting as splint oligonucleotides for a heterogeneous population of SSB-bound ssNA having terminal regions of undetermined sequence.

In some embodiments, the SSB-bound ssNA hybridization region includes a known sequence designed to hybridize to a SSB-bound ssNA terminal region of known sequence. In certain aspects, two or more heterogeneous splint oligonucleotides having different SSB-bound ssNA hybridization regions of known sequence designed to hybridize to respective SSB-bound ssNA terminal regions of known sequence are employed. Embodiments in which the SSB-bound ssNA hybridization regions have a known sequence find use, e.g., when it is desirable to produce a nucleic acid library from only a subset of SSB-bound ssNAs having terminal regions of known sequence. Accordingly, in certain aspects, the methods include forming the complexes by combining the SSB-bound ssNA, an adapter oligonucleotide, and one or more heterogeneous splint oligonucleotides having one or more different SSB-bound ssNA hybridization regions of known sequence capable of acting as splint oligonucleotides for one or more SSB-bound ssNAs having one or more terminal regions of known sequence.

In certain aspects, the SSB-bound ssNA hybridization region includes one or more universal bases. As used herein, a "universal base" is a base capable of indiscriminately base pairing with each of the four standard nucleotide bases: A, C, G and T. Universal bases that may be incorporated into the SSB-bound ssNA hybridization region include, but are not limited to, 2'-deoxyinosine (dI, dInosine) and 5-nitroindole.

The manner in which the SSB-bound ssNA, the adapter oligonucleotide, and the splint oligonucleotide are combined may vary. In some embodiments, the combining includes combining a complex including the splint oligonucleotide hybridized to the adapter oligonucleotide via the adapter oligonucleotide hybridization region, and the SSB-bound ssNA. In other aspects, the combining includes combining a complex including the splint oligonucleotide hybridized to the SSB-bound ssNA via the SSB-bound ssNA hybridization region, and the adapter oligonucleotide. In still other aspects, the combining includes combining the SSB-bound ssNA, the adapter oligonucleotide, and the splint oligonucleotide, where none of the three components are pre-complexed with (that is—hybridized to) another component prior to the combining.

The combining is carried out under hybridization conditions such that complexes including the splint oligonucleotide hybridized to a terminal region of the SSB-bound ssNA via the SSB-bound ssNA hybridization region, and the splint oligonucleotide hybridized to the adapter oligonucleotide via the adapter oligonucleotide hybridization region. Whether specific hybridization occurs is determined by such factors as the degree of complementarity between the relevant (that is, hybridizing) regions of the splint oligonucleotide, the terminal region of the SSB-bound ssNA, and the adapter oligonucleotide, as well as the length thereof, salt concentration, and the temperature at which the hybridization occurs, which may be informed by the melting temperatures ($T_M$) of the relevant regions. The melting temperature refers to the temperature at which half of the relevant regions remain hybridized and half of the relevant regions dissociate into single strands. The Tm of a duplex may be experimentally determined or predicted using the following formula Tm=81.5+16.6(log 10[Na$^+$])+0.41 (fraction G+C)−(60/N), where N is the chain length and [Na$^+$] is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict Tm of relevant regions depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

The terms "complementary" or "complementarity" as used herein refer to a nucleotide sequence that base-pairs by non-covalent bonds to a region of a target nucleic acid, e.g., the nucleotide sequence of the SSB-bound ssNA hybridization region that hybridizes to the terminal region of the SSB-bound ssNA, and the nucleotide sequence of the adapter oligonucleotide hybridization region that hybridizes to the probe complement oligonucleotide. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" or "complementarity" refers to a nucleotide sequence that is at least partially complementary. These terms may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, the SSB-bound ssNA hybridization region may be perfectly (i.e., 100%) complementary to the terminal region of the SSB-bound ssNA, or the SSB-bound ssNA hybridization region may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., *Proc. Natl. Acad. Sci. USA* 90:5873-5877 (1993). Such an algorithm is incorporated into the NBLAST and XBLAST programs (version 2.0) as described in Altschul et al., *Nucleic Acids Res.* 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

The complexes are formed such that an end of the adapter oligonucleotide is adjacent to an end of the terminal region of the SSB-bound ssNA. By "adjacent to" is meant the terminal nucleotide at the end of the adapter oligonucleotide and the terminal nucleotide end of the terminal region of the SSB-bound ssNA are sufficiently proximal to each other that the terminal nucleotides may be covalently linked, e.g., by chemical ligation, enzymatic ligation, or the like. In some embodiments, the ends are adjacent to each other by virtue of the terminal nucleotide at the end of the adapter oligonucleotide and the terminal nucleotide end of the terminal region of the SSB-bound ssNA being hybridized to adjacent nucleotides of the splint oligonucleotide. The splint oligonucleotide may be designed to ensure that the an end of the adapter oligonucleotide is adjacent to an end of the terminal region of the SSB-bound ssNA. Non-limiting examples of such splint oligonucleotides are provided in the Experimental section herein.

Any of the methods described herein may further include covalently linking the adjacent ends of an adapter oligonucleotide and SSB-bound ssNA. The covalent linking may include ligating the adjacent ends. Ligating the adjacent ends may be carried out using any suitable approach. In certain aspects, the ligating is by chemical ligation. In other aspects, the ligating is by enzymatic ligation. Suitable reagents (e.g., ligases and corresponding buffers, etc.) and kits for performing enzymatic ligation reactions are known and available, e.g., the Instant Sticky-end Ligase Master Mix available from New England Biolabs (Ipswich, MA). Ligases that may be employed include, e.g., T4 DNA ligase (e.g., at low or high concentration), T7 DNA ligase, T7 DNA Ligase, *E. coli* DNA Ligase, Electro Ligase®, or the like. Conditions suitable for performing the ligation reaction will vary depending upon the type of ligase used. Information regarding such conditions is readily available. When necessary, a phosphate group may be added at the 5' end of the adapter oligonucleotide or SSB-bound ssNA using, e.g., a suitable kinase, such as T4 polynucleotide kinase (PNK). Such kinases and guidance for using such kinases to phosphorylate 5' ends are available, e.g., from New England BioLabs, Inc. (Ipswich, MA).

In some embodiments, the splint oligonucleotide, the adapter oligonucleotide, or both, includes a blocking modification. For example, one or both ends of the splint oligonucleotide may include a blocking modification and/or the end of the adapter oligonucleotide not adjacent to the SSB-bound ssNA may include a blocking modification. By "blocking modification" is meant the end is not competent for being linked to the end of any other oligonucleotide components using an approach employed to covalently link the adjacent ends of the adapter oligonucleotide and SSB-bound ssNA. In certain aspects, the blocking modification is a ligation-blocking modification. Examples of blocking modifications which may be included at one or both ends of the splint oligonucleotide and/or the end of the adapter oligonucleotide not adjacent to the SSB-bound ssNA, include the absence of a 3' OH at the end of the adapter oligonucleotide not adjacent to the SSB-bound ssNA, and an inaccessible 3' OH at the end of the adapter oligonucleotide not adjacent to the SSB-bound ssNA. Non-limiting examples of blocking modifications in which an end has an inaccessible 3' OH include: an amino modifier, a spacer, a dideoxy base, an inverted dideoxy base, a 3' phosphate, or the like.

In certain aspects, the splint oligonucleotide, the adapter oligonucleotide, or both, includes one or more non-natural nucleotides (which may also be referred to as nucleotide analogs). Non-limiting examples of non-natural nucleotides that may be included in the splint oligonucleotide, the adapter oligonucleotide, or both are LNA (locked nucleic acid), PNA (peptide nucleic acid), FANA (2'-deoxy-2'-fluoroarabinonucleotide), GNA (glycol nucleic acid), TNA (threose nucleic acid), 2'-O-Me RNA, 2'-fluoro RNA, Morpholino nucleotides, and any combination thereof.

Covalently linking the adjacent ends of an adapter oligonucleotide and SSB-bound ssNA produces adapted ssNA, where "adapted" means the ssNA now includes one or more adapter sequences or subregions thereof. The adapted ssNA may be purified before being used as input in a downstream application of interest. For example, the complexes may be denatured (e.g., heat-denatured) to separate the adapted ssNA from the splint oligonucleotides, the adapted ssNA may be purified from the SSB and/or any other components present during the contacting and/or combining steps (e.g., by solid phase reversible immobilization (SPRI), column purification, and/or the like), or combinations thereof.

In some embodiments, the one or more adapter sequences or subregions thereof is one or more sequencing adapters or subregions thereof, and the methods further include sequencing at least a portion of the adapted ssNA, or any derivative thereof (e.g., amplicons produced by PCR amplification using the adapted ssNA as template). The sequencing may be carried out on any suitable sequencing platform, including a high-throughput sequencing (HTS) (or "next-generation sequencing (NGS)") platform, or the like. HTS/NGS sequencing platforms of interest include, but are not limited to, a sequencing platform provided by Illumina® (e.g., the HiSeq™, MiSeq™ and/or Genome Analyzer™ sequencing systems); Oxford Nanopore™ Technologies (e.g., a MinION™, GridIONx5™, PromethION™, or SmidgION™ nanopore-based sequencing system), Ion Torrent™ (e.g., the Ion PGM™ and/or Ion Proton™ sequencing systems); Pacific Biosciences (e.g., a Sequel or PacBio RS II sequencing system); Life Technologies™ (e.g., a SOLiD sequencing system); Roche (e.g., the 454 GS FLX+ and/or GS Junior sequencing systems); or any other sequencing platform of interest. Detailed protocols for direct sequencing (e.g., by nanopore-based sequencing) or preparing compatible nucleic acid molecules for sequencing on a particular platform (e.g., by amplification, e.g., solid-phase amplification, or the like), sequencing the compatible molecules, and analyzing the sequencing data are available from the manufacturer of the sequencing platform of interest.

As summarized above, the methods of the present disclosure constitute an improvement of current state-of-the-art approaches to single-stranded library preparation, such as the approach (designated "ssDNA2.0") described by Gansauge et al. (2017) *Nucleic Acids Research* 45(10):e79, where the present methods were surprisingly found to be more efficient, require less time, and reduce costs. In some embodiments, when the methods include covalently linking the adjacent ends of an adapter oligonucleotide and SSB-bound ssNA, the total duration of the combining and covalently linking steps is 4 hours or less, 3 hours or less, 2 hours or less, or 1 hour or less. In certain aspects, when the methods include covalently linking the adjacent ends of an adapter oligonucleotide and SSB-bound ssNA, the total duration of the contacting, combining and covalently linking steps is 4 hours or less, 3 hours or less, 2 hours or less, or 1 hour or less. In some embodiments, the efficiency of the methods is such that complexes are formed from 70% or more, 75% or more, 80% or more, 85% or more, 90% or more, 95% or more, or 99% or more of the ssNA contacted with the SSB during the contacting step.

Compositions

As summarized above, the present disclosure also provides compositions. The compositions find use in a variety of applications, including, e.g., practicing any of the methods of the present disclosure, including carrying out one or more of any of the steps described above in the Methods section of the present disclosure. As such, the compositions may include any of the oligonucleotides (including pluralities/collections of heterogeneous oligonucleotides), ssNA, SSB, other reagents, etc. described above in the Methods section of the present disclosure, in any combination.

In certain aspects, provided are compositions that include SSB-bound ssNA, a first adapter oligonucleotide, and a first splint oligonucleotide including an SSB-bound ssNA hybridization region and a first adapter oligonucleotide hybridization region. Such compositions may further include a second adapter oligonucleotide and a second splint oligonucleotide including an SSB-bound ssNA hybridization region and a second adapter oligonucleotide hybridization region.

In certain aspects, provided are compositions that include complexes including a splint oligonucleotide hybridized to an adapter oligonucleotide via the adapter oligonucleotide hybridization region, present as hybridized complexes (e.g., in the absence of SSB-bound ssNA). In other aspects, provided are compositions that include complexes including a splint oligonucleotide hybridized to SSB-bound ssNA via the SSB-bound ssNA hybridization region, present as hybridized complexes.

The ssNA may be ssDNA. When the ssNA is ssDNA, the ssDNA may be derived from dsDNA. In some embodiments, the ssNA is ssRNA. In some embodiments, the ssNA is from a degraded nucleic acid sample. In certain aspects, when the ssNA is from a degraded nucleic acid sample, the ssNA is from an ancient nucleic acid sample, such as a nucleic acid sample obtained (e.g., isolated) from an extinct organism or animal, e.g., an extinct mammal. In certain aspects, the extinct mammal is from the genus *Homo*. In some embodiments, the ssNA is from a forensic nucleic acid sample.

The compositions of the present disclosure may further include a reagent for covalently linking an adapter oligonucleotide end to an end of the SSB-bound ssNA. In some embodiments, the reagent is a chemical ligation reagent or an enzymatic ligation reagent, e.g., a ligase.

The compositions of the present disclosure may include the one or more components present in a container. Suitable containers include, but are not limited to, tubes, vials, and plates (e.g., a 96- or other-well plate).

In certain aspects, the compositions include the one or more components in a liquid medium. The liquid medium may be an aqueous liquid medium, such as water, a buffered solution, and the like. One or more additives such as a salt (e.g., NaCl, MgCl$_2$, KCl, MgSO$_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), a nuclease inhibitor, glycerol, a chelating agent, and the like may be present in such compositions.

Kits

As summarized above, the present disclosure provides kits. The kits find use in a variety of applications, including, e.g., practicing any of the methods of the present disclosure, including carrying out one or more of any of the steps described above in the Methods section of the present disclosure. As such, the kits may include any of the oligonucleotides (including pluralities/collections of heterogeneous oligonucleotides), ssNA, SSB, other reagents, etc. described above in the Methods section of the present disclosure, in any combination.

In some embodiments, a kit of the present disclosure includes single-stranded nucleic acid binding protein (SSB), e.g., single-stranded DNA binding protein, single-stranded RNA binding protein, or both), a first adapter oligonucleotide, a first splint oligonucleotide comprising an SSB-bound ssNA hybridization region and a first adapter oligonucleotide hybridization region, and instructions for using the SSB, first adapter oligonucleotide, and first splint oligonucleotide to produce a nucleic acid library. In certain aspects, such a kit further includes a second adapter oligonucleotide, and a second splint oligonucleotide including an SSB-bound ssNA hybridization region and a second adapter oligonucleotide hybridization region, where the instructions are for using the SSB, first adapter oligonucleotide, first splint oligonucleotide, second adapter oligonucleotide, and second splint oligonucleotide to produce a nucleic acid library.

The kits of the present disclosure may further include a reagent for covalently linking an adapter oligonucleotide end to an end of SSB-bound ssNA. In some embodiments, the reagent is a chemical ligation reagent or an enzymatic ligation reagent, e.g., a ligase.

In some embodiments, a splint oligonucleotide, an adapter oligonucleotide, or both, includes a blocking modification. For example, one or both ends of the splint oligonucleotide may include a blocking modification and/or the end of the adapter oligonucleotide not adjacent to the SSB-bound ssNA may include a blocking modification. In certain aspects, the blocking modification is a ligation-blocking modification. Examples of blocking modifications which may be included at one or both ends of the splint oligonucleotide and/or the end of the adapter oligonucleotide not adjacent to the SSB-bound ssNA, include the absence of a 3' OH at the end of the adapter oligonucleotide not adjacent to the SSB-bound ssNA, and an inaccessible 3' OH at the end of the adapter oligonucleotide not adjacent to the SSB-bound ssNA. Non-limiting examples of blocking modifications in which an end has an inaccessible 3' OH include: an amino modifier, a spacer, a dideoxy base, an inverted dideoxy base, a 3' phosphate, or the like.

In some embodiments, one or more splint oligonucleotides provided in a kit of the present disclosure includes an SSB-bound ssNA hybridization region that includes (e.g., consists of) a random nucleotide sequence, such that when the kit includes a plurality of heterogeneous splint oligonucleotides having various random SSB-bound ssNA hybridization regions, the collection is capable of acting as splint oligonucleotides for a heterogeneous population of SSB-bound ssNAs irrespective of the sequences of the terminal regions of the SSB-bound ssNAs of interest.

In certain aspects, a splint oligonucleotide provided in a kit of the present disclosure includes an SSB-bound ssNA hybridization region that includes one or more universal bases. Universal bases that may be incorporated into the SSB-bound ssNA hybridization region include, but are not limited to, 2'-deoxyinosine (dI, dInosine) and 5-nitroindole.

In some embodiments, the length of the SSB-bound ssNA hybridization region of a splint oligonucleotide provided in a kit of the present disclosure is 10 nucleotides or less. In certain aspects, the SSB-bound ssNA hybridization region is from 4 to 20 nucleotides in length, e.g., from 5 to 15, 5 to 10, 5 to 9, 5 to 8, or 5 to 7 (e.g., 6 or 7) nucleotides in length.

Components of the subject kits may be present in separate containers, or multiple components may be present in a single container. A suitable container includes a single tube (e.g., vial), one or more wells of a plate (e.g., a 96-well plate, a 384-well plate, etc.), or the like.

The instructions for using the SSB, one or more adapter oligonucleotides, and one or more splint oligonucleotides to produce a nucleic acid library may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging), etc. In other embodiments, the instructions are present as an electronic storage data file present on a suitable computer-readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

The following examples are offered by way of illustration and not by way of limitation.

Experimental

Example 1

Disclosed herein is an approach for fast, efficient, and targeted ligation of adapters to single stranded DNA in one reaction. In the following examples, sequencing adapter oligonucleotides containing Illumina P7 or P5 adapter sequences are hybridized to a splint oligonucleotide containing a string of 3-prime Ns for the P7 splint and a string of 5-prime Ns for the P5 splint. The splint creates an opportunity for ligases that can only perform double strand ligation with high efficiency to ligate the adapters to the target single-stranded DNA. All oligonucleotide DNA ends that are not needed to participate in ligation are blocked by oligonucleotide modifications (e.g., amino modifications) that prevent ligation.

The addition of single-stranded binding proteins (SSBs) to the assay increases the efficiency of the reaction. The concentration and length of the target DNA is used to calculate appropriate amounts of SSB to achieve optimal ligation efficiency. The SSBs may prevent single-stranded DNA from re-annealing while preventing secondary structures.

This method can be favorably compared to a single-stranded library preparation described by Gansauge et al. (2017) *Nucleic Acids Research* 45(10):e79, known as SS2.0. Compared to SS2.0, the present method requires significantly less time and exhibits significantly increased efficiency of conversion of DNA into proper adapter-ligated DNA molecules that can be sequenced. In addition, the present approach reduces reagent costs compared to SS2.0.

The adapter and splint oligonucleotides are engineered to carry a ligation-blocking modification on all ends that should not participate in proper adapter ligation. This includes blocking the 5-prime end for the P5 adapter and the 3-prime end of the P7 adapter and all ends of the splint. These ligation-blocking modifications may be amino modifiers, carbon spacers, dideoxy bases, or any other suitable modifications that prevent access of a ligase to the 3-prime hydroxyl group of the 3-prime end or the 5-prime phosphate of the 5-prime end. Oligonucleotides may be synthesized, e.g., by Integrated DNA Technologies (IDT). Example oligonucleotides are shown in Table 1 below.

TABLE 1

| Example Oligonucleotides | |
|---|---|
| P5 Adapter (5' → 3') SEQ ID NO: 1 | /5AmMC12/ACACTCTTTCCCTACACGACGCTCTTCCGATCT |
| P5 Splint (5' → 3') SEQ ID NO: 2 | /5AmMC6/NNNNNNNNAGATCGGAAGAGCGTCGTGTAGGGAAAGAGTGT/3AmMO/ |
| P7 Adapter (5' → 3') SEQ ID NO: 3 | /5Phos/AGATCGGAAGAGCACACGTCTGAACTCCAGTCA/3ddC/ |
| P7 Splint (5' → 3') SEQ ID NO: 4 | /5AmMC12/GTGACTGGAGTTCAGACGTGTGCTCTTCCGATCTNNNNNNN/3AmMO/ |

/5AmMC12/ = 5' Amino Modifier C12
/5AmMC6/ = 5' Amino Modifier C6
/3AmMO/ = 3' Amino Modifier
/5Phos/ = 5' Phosphate
/3ddC/ = 3' Dideoxy Cytosine In the protocol employed in this Example, template DNA was combined with SSBs and heat denatured. After denaturation, the reactions were placed on ice or a PCR cooler at 4° C. After cooling, adapters were added to each reaction. Then, the reaction master mix is added, followed by mixing. Incubation at 37° C. allows for ligation to begin immediately with most ligation occurring before 45 minutes. Reactions can be cleaned up with established methods and downstream applications such as amplification and sequencing remain unchanged.

To prepare the adapters, combined were P5 adapter to a final concentration of 10 uM and P5 splint oligonucleotide to a final concentration of 20 μM with 1× final concentration of T4 RNA Ligase Buffer (Cat #B0216L). A similar, separate mixture was prepared using the P7 adapter and P7 splint oligonucleotide. Adapters were hybridized by heating to 95° C. for 10 seconds and then ramped down to 10° C. at a rate of 0.1° C./s.

An example protocol is provided below.
1. Sample input (36 uL)
  a. Combine sheared DNA and ET SSB (Cat #M2401S) to a volume of 36 uL
    i. 1 uL of ET SSB promotes ligation without inhibiting for most sample types tested
    ii. Fill remaining volume with buffer EBT (10 mM Tris-HCl, pH 8.0 and 0.05% Tween 20)
2. Denature sample
  a. Incubate samples in a thermocycler with a lid pre-heated to 95° C. for 3 minutes
  b. Immediately place denatured sample on ice or a PCR cooler for 30 seconds.
3. Add 2 uL of pooled adapter mixes (equal volume P5 and P7 adapters)
  a. Adapter input will depend on the molarity of the input. A molar ratio between 6 and 10 to 1, adapters to template, is preferred.
4. Add reaction master mix and mix thoroughly by pipetting
  a. 8 uL of T4 DNA Ligase Buffer (Cat #M0202M)
  b. 32 uL of 50% PEG 8000 (Cat #B0216L)
  c. 1 uL of T4 Polynucleotide Kinase—10,000 U/mL (Cat #M0201L)
  d. 1 uL of T4 DNA Ligase—2,000,000 U/mL (Cat #M0202M)
5. Incubate at 37° C. for up to 60 minutes a. Most ligation occurs in the first 15 minutes but the plateau isn't achieved until around 45 minutes.

6. Clean up reaction a. Column cleanup (e.g., for degraded DNA) or SPRI (e.g., for modern samples).

Comparison and Optimization Assay

After clean up, qPCR was performed on a dilution of pre-amplified libraries to determine ligation efficiency. A lower CT value indicates greater ligation efficiency relative to another sample on the same run with a higher CT value. A difference of one is roughly equal to a two-fold difference in library efficiency. An aliquot of the pre-amplified libraries was also amplified with an index PCR reaction. Post-indexing, the libraries were cleaned with SPRI and visualized on an Agilent TapeStation 2200 system to estimate the proportion of adapter artifacts in each library.

Single-Stranded Binding Proteins

It was observed that single-stranded binding protein (SSB) such as ET SSB protein supplied by NEB enhances the ligation efficiency of single-stranded ligation. Given equal molarity inputs, samples with higher average fragment lengths required a greater input of SSB to achieve peak ligation. The molarity of DNA in the reaction also affects the amount of SSB required. In vast excess ET SSB has the potential to inhibit ligation.

Protocol Comparison

The efficiency of the present protocol was compared to the NEB Ultra 2 kit (dsDNA), SS2.0 (Gansauge et al. (2017) *Nucleic Acids Research* 45(10):e79), and the blunt end single tube (BEST) method described in Caroe et al. (2017) *Methods in Ecology and Evolution* 9(2):410-419; and Mak et al. (2017) *GigaScience* 6:1-13. Comparison results were obtained using modern human DNA with an average fragment length of about 350 bp and an ancient bison sample that is heavily degraded with an average fragment length of about 35-40 bp.

The NEB Ultra 2 kit is recognized as a highly efficient library preparation method for modern samples while SS2.0 is recognized as a highly efficient library preparation method for degraded samples. The BEST protocol involves blunt end repair using T4 DNA Polymerase and T4 PNK to blunt end the DNA (no tailing) and phosphorylate 5' ends. Next, blunt end dsDNA adapters are ligated to the blunt ends using T4 DNA Ligase, followed by a fill-in reaction using Bst 2.0 Warmstart polymerase and clean-up using SPRI beads or a column.

Figure 2:
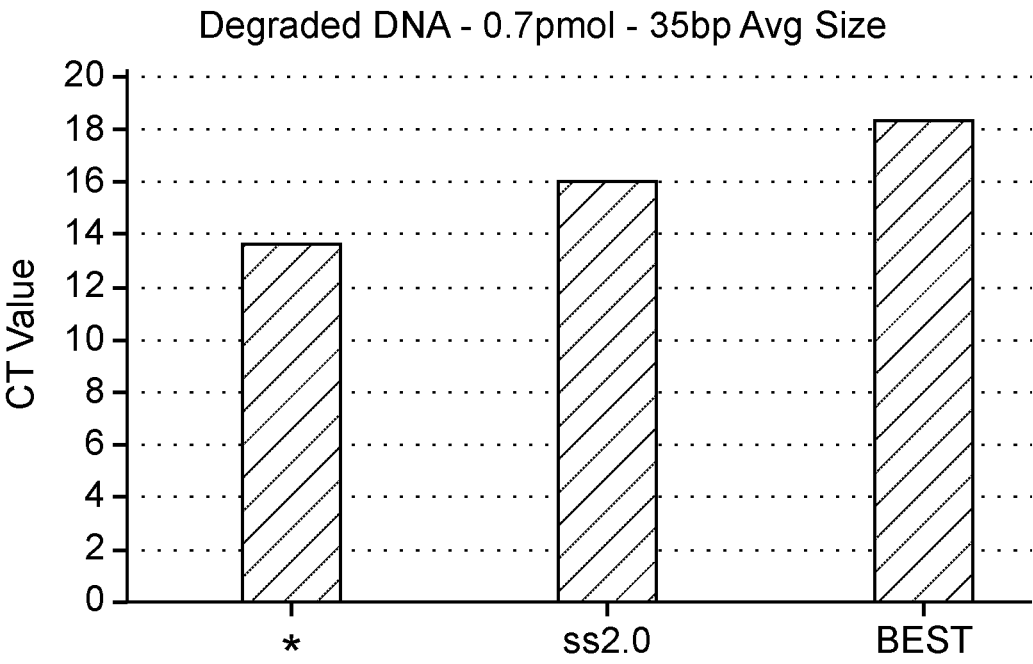
FIG. 2. Comparison of an example method of the present disclosure to other methods for degraded DNA (top panel) and modern DNA (bottom panel).
Figure 2:
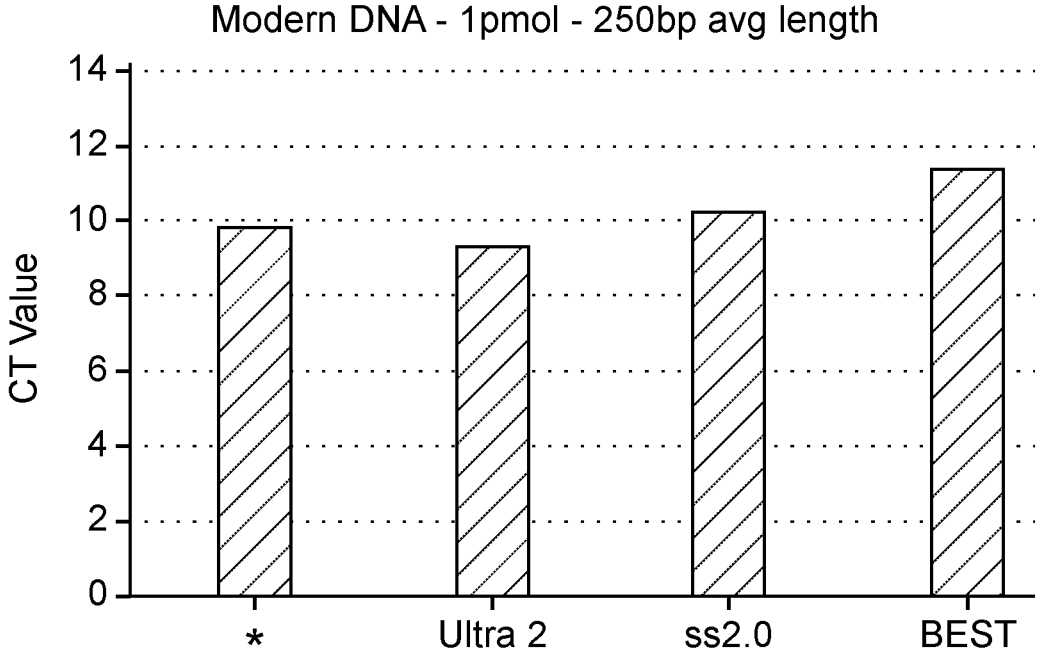

Comparison results are provided in FIG. 2. From left to right on the top panel are: the method described in this example (asterisk), ss2.0, and BEST. From left to right on the bottom panel are: the method described in this example (asterisk), the NEB Ultra 2 kit, ss2.0, and BEST. The method described in this example exhibits far greater ligation efficiency for ancient samples compared to ss2.0. For modern samples, the method described in this example is between 0.3 and 0.5 qPCR cycles behind the NEB Ultra 2 Kit.

Example 2—Hair DNA

DNA was collected from hair using a standard Proteinase K treatment at high temperature. 6 nanograms of DNA was used as template for making the library. The protocol was followed as described above. Two sequencing libraries were produced from the adapter-ligated product. One used 1 μL of the 504 total ligation product (SRL3). The other used 2.5 μL of this product (SRL4). Both libraries were sequenced on the Illumina MiSeq sequencing platform to assess the library characteristics and complexity (number of unique library molecules).

Figure 3:
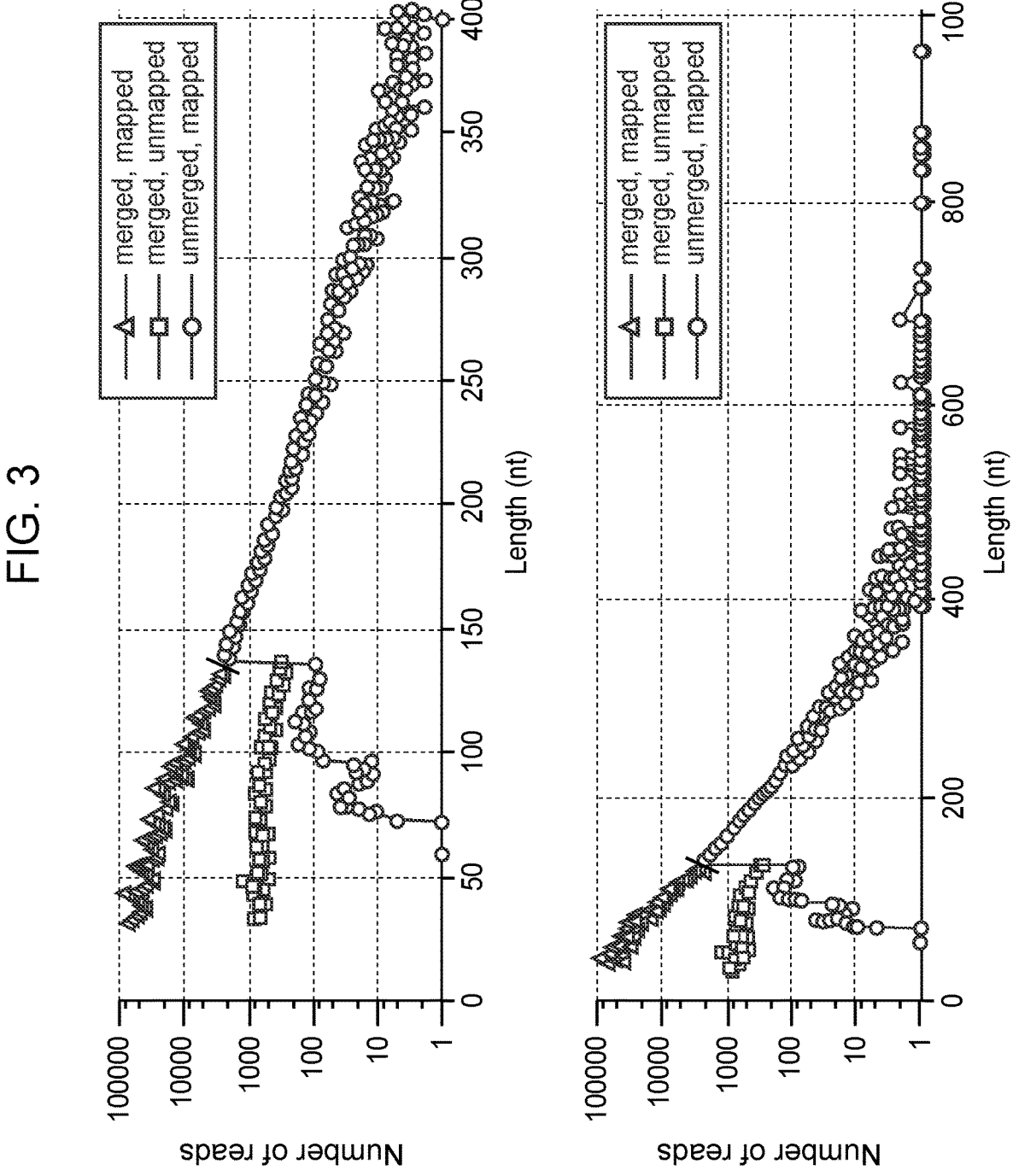
FIG. 3. Hair DNA length distribution. Left panel shows the observed length of template molecules produced by the Santa Cruz method (SRL3) from modern hair DNA. As expected for DNA in hair shafts, the lengths of intact molecules is generally short. A similar length distribution is shown in the right panels (SRL4).
Figure 3:
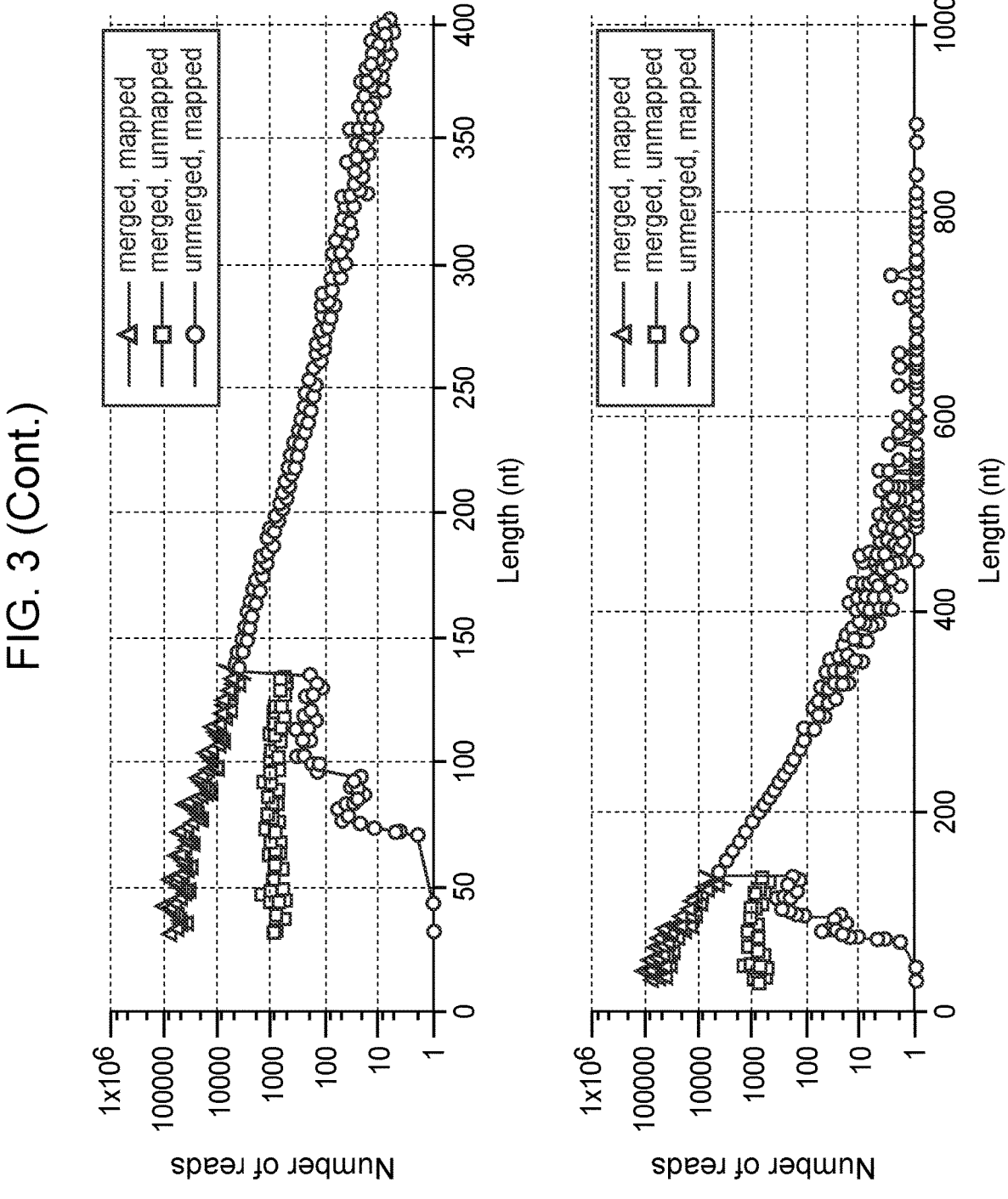

After 2×75 paired-end sequencing, the SeqPrep program was used to combine the forward and reverse read pairs that overlap with one another. This occurs when the original DNA template is short enough such that the forward read and the reverse read cover some of the same sequence (referred to herein as "merged reads"). After merging, merged and unmerged reads were mapped to the reference human genome sequence. Shown in FIG. 3 is the observed original template length distribution of the merged & mapped, merged and unmapped, and merged and unmapped reads for both SRL3 and SRL4 libraries. Note that for unmerged and unmapped, it is not possible to infer the length of the template DNA.

Figure 4:
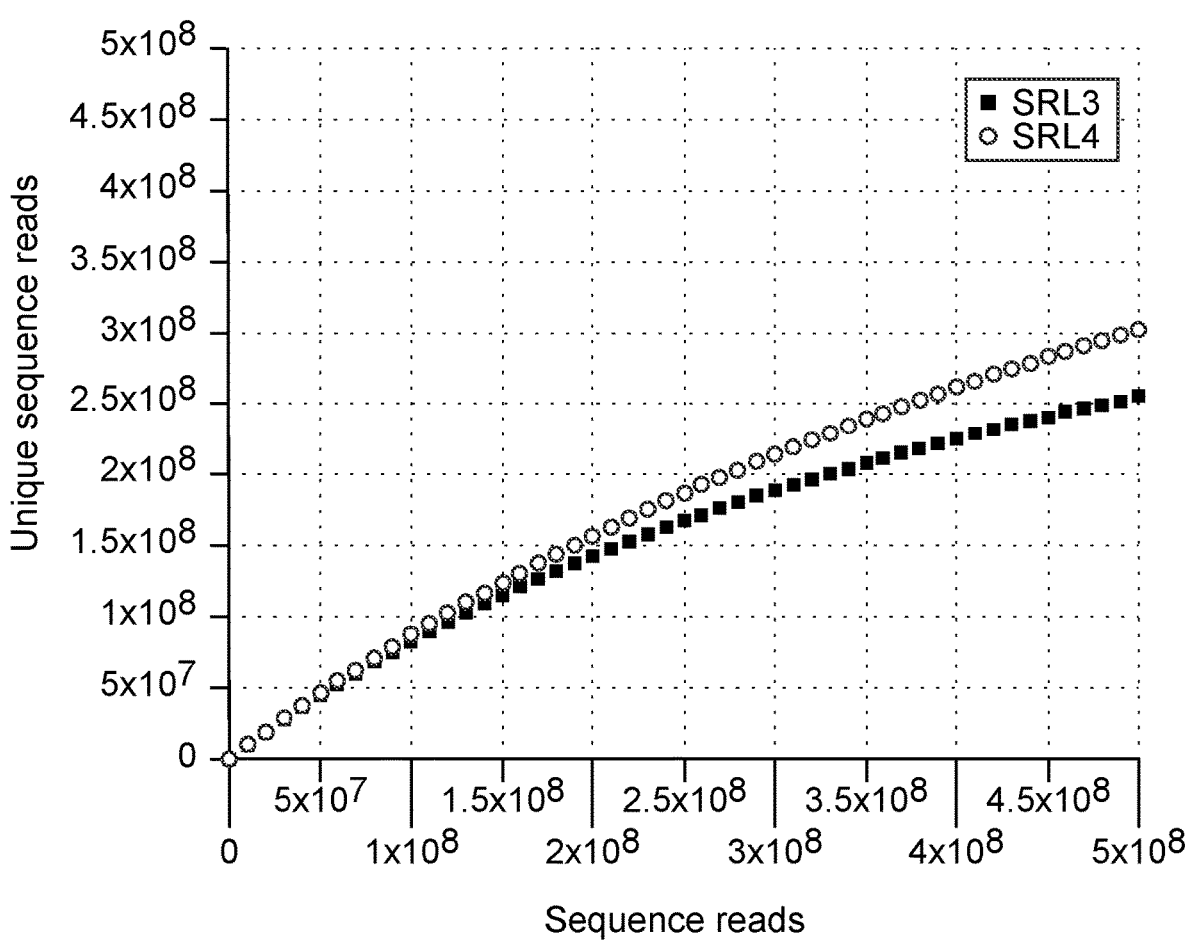
FIG. 4. Estimated library complexity (number of unique molecules) in SRL3 and SRL4.

The Preseq software program was used to estimate the number of unique library molecules in both libraries. This program counts the number of observed duplicate molecules to model the complexity of the nucleic acid library from a large sample of observed reads, as produced here. This program shows an estimate for the fraction of observed reads that are predicted to be unique at various depths of library sequencing. As shown in FIG. 4, both libraries are predicted to have complexity of over 250,000,000 unique molecules. SRL4, which was made from 2.5 μL of the adapter-ligated template has more unique molecules than SRL3.

Example 3—Ancient DNA from Bison Bone

The efficiency of conversion from template DNA molecules to sequencing library was compared using DNA extracted from an ancient bison bone. Libraries were generated from the same amount of DNA from the same extract using four different protocols, including the protocol as described above.

Figure 5:
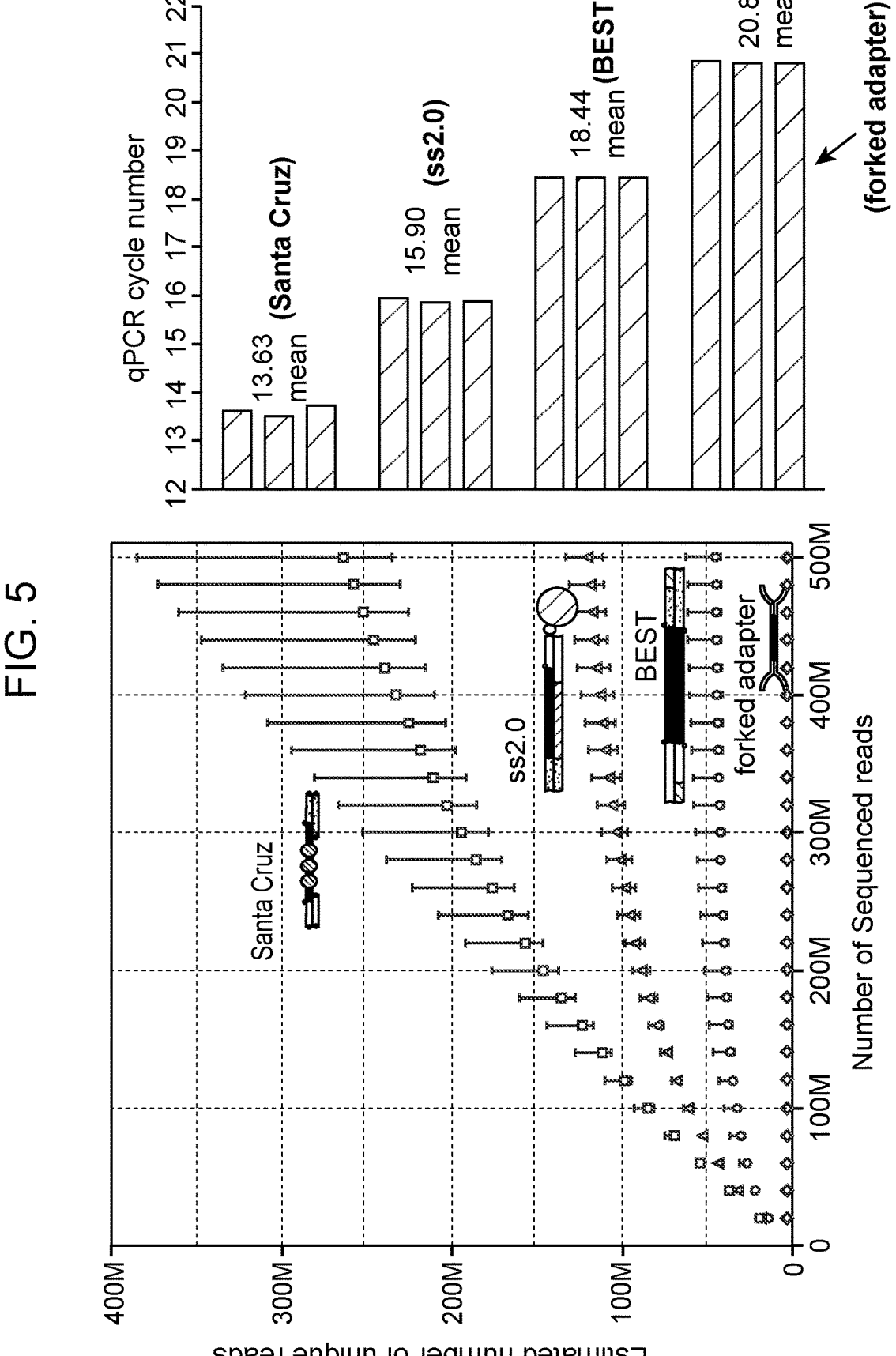
FIG. 5. Library complexity comparison. Sequencing libraries were made using an example method of the present disclosure, SS2.0, BEST, and forked adapter ligation. Library complexity (the number of unique molecules in the library) was estimated from several million reads using Preseq (left) or via qPCR (right) in triplicate experiments. The example method of the present disclosure converts 2 to 3 times more of the extract DNA into sequencing libraries than the next best protocol, SS2.0.

The complexity of the libraries was measured using two approaches: qPCR of the adapter-ligated product and direct sequencing. The qPCR estimates were done in triplicate. Both approaches, shown in FIG. 5, demonstrate that the approach described herein is more efficient at converting DNA into sequencing libraries.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A composition, comprising:
a complex comprising:
    single-stranded nucleic acid binding protein-bound single-stranded nucleic acid (SSB-bound ssNA);
    a first adapter oligonucleotide;
    a first splint oligonucleotide comprising an SSB-bound ssNA hybridization region and a first adapter oligonucleotide hybridization region, wherein the first adapter oligonucleotide and the first adapter oligonucleotide hybridization region are the same length;
    a second adapter oligonucleotide; and
    a second splint oligonucleotide comprising an SSB-bound ssNA hybridization region and a second adapter oligonucleotide hybridization region, wherein the second adapter oligonucleotide and the second adapter oligonucleotide hybridization region are the same length,
    wherein the complex comprises:
        the first splint oligonucleotide hybridized to a terminal region of the SSB-bound ssNA via the SSB-bound ssNA hybridization region, and the first splint oligonucleotide hybridized to the first adapter oligonucleotide via the first adapter oligonucleotide hybridization region, such that an end of the first adapter oligonucleotide is adjacent to an end of the terminal region of the SSB-bound ssNA, wherein the end of the first adapter oligonucleotide not adjacent to the SSB-bound ssNA comprises a ligation-blocking modification; and
        the second splint oligonucleotide hybridized to the terminal region of the SSB-bound ssNA not hybridized to the first splint oligonucleotide via the SSB-bound ssNA hybridization region of the second splint oligonucleotide, and the second splint oligonucleotide hybridized to the second adapter oligonucleotide via the second adapter oligonucleotide hybridization region, such that an end of the second adapter oligonucleotide is adjacent to the end of the terminal region of the SSB-bound ssNA hybridized to the second splint oligonucleotide, wherein the end of the second adapter oligonucleotide not adjacent to the SSB-bound ssNA hybridized to the second splint oligonucleotide comprises a ligation-blocking modification.

2. The composition of claim 1, further comprising a ligase.

3. The composition of claim 1, wherein the adjacent ends of the first adapter oligonucleotide and SSB-bound ssNA are covalently linked.

4. The composition of claim 3, wherein the adjacent ends of the second adapter oligonucleotide and SSB-bound ssNA hybridized to the second splint oligonucleotide are covalently linked.

5. The composition of claim 1, wherein the ligation-blocking modification comprises the absence of a 3' OH at the end of the first adapter oligonucleotide not adjacent to the SSB-bound ssNA and/or the absence of a 3' OH at the end of the second adapter oligonucleotide not adjacent to the SSB-bound ssNA.

6. The composition of claim 1, wherein the ligation-blocking modification comprises an inaccessible 3' OH at the end of the first adapter oligonucleotide not adjacent to the SSB-bound ssNA and/or an inaccessible 3' OH at the end of the second adapter oligonucleotide not adjacent to the SSB-bound ssNA.

7. The composition of claim 6, wherein the ligation-blocking modification comprising the inaccessible 3' OH at the end of the first adapter oligonucleotide not adjacent to the SSB-bound ssNA and/or at the end of the second adapter oligonucleotide not adjacent to the SSB-bound ssNA comprises an amino modifier.

8. The composition of claim 6, wherein the ligation-blocking modification comprising the inaccessible 3' OH at the end of the first adapter oligonucleotide not adjacent to the SSB-bound ssNA and/or at the end of the second adapter oligonucleotide not adjacent to the SSB-bound ssNA comprises a spacer.

9. The composition of claim 6, wherein the ligation-blocking modification comprising the inaccessible 3' OH at the end of the first adapter oligonucleotide not adjacent to the SSB-bound ssNA and/or at the end of the second adapter oligonucleotide not adjacent to the SSB-bound ssNA comprises a dideoxy base.

10. The composition of claim 6, wherein the ligation-blocking modification comprising the inaccessible 3' OH at the end of the first adapter oligonucleotide not adjacent to the SSB-bound ssNA and/or at the end of the second adapter oligonucleotide not adjacent to the SSB-bound ssNA comprises an inverted dideoxy base.

11. The composition of claim 6, wherein the ligation-blocking modification comprising the inaccessible 3' OH at the end of the first adapter oligonucleotide not adjacent to the SSB-bound ssNA and/or at the end of the second adapter oligonucleotide not adjacent to the SSB-bound ssNA comprises a 3' phosphate.

12. The composition of claim 1, wherein the ssNA is single-stranded DNA.

13. The composition of claim 12, wherein the single-stranded DNA is single-stranded genomic DNA.

14. The composition of claim 1, wherein the ssNA is RNA.

15. The composition of claim 13, wherein the RNA is messenger RNA (mRNA).

* * * * *